United States Patent
Akiba

(10) Patent No.: US 11,678,796 B2
(45) Date of Patent: Jun. 20, 2023

(54) BLOOD FLOW MEASUREMENT APPARATUS

(71) Applicant: KABUSHIKI KAISHA TOPCON, Tokyo (JP)

(72) Inventor: Masahiro Akiba, Toda (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 930 days.

(21) Appl. No.: 16/591,905

(22) Filed: Oct. 3, 2019

(65) Prior Publication Data

US 2020/0029809 A1    Jan. 30, 2020

Related U.S. Application Data

(63) Continuation of application No. 15/536,461, filed as application No. PCT/JP2015/080969 on Nov. 2, 2015, now abandoned.

(30) Foreign Application Priority Data

Dec. 19, 2014    (JP) .................................. 2014-257033

(51) Int. Cl.
*A61B 3/12* (2006.01)
*A61B 5/00* (2006.01)
*A61B 5/026* (2006.01)
*A61B 3/10* (2006.01)
*G01N 21/17* (2006.01)
(Continued)

(52) U.S. Cl.
CPC ................ *A61B 3/12* (2013.01); *A61B 3/102* (2013.01); *A61B 5/0261* (2013.01); *G01N 21/17* (2013.01); *A61B 3/117* (2013.01); *A61B 3/14* (2013.01); *A61B 5/0066* (2013.01)

(58) Field of Classification Search
None
See application file for complete search history.

(56) References Cited

U.S. PATENT DOCUMENTS 9,492,082 B2    11/2016    Yoshida et al.
2009/0005691 A1    1/2009    Huang et al.
(Continued)

FOREIGN PATENT DOCUMENTS

JP    2009-165710 A    7/2009
JP    2010-523286 A    7/2010
(Continued)

OTHER PUBLICATIONS

International Search Report and Written Opinion dated Feb. 9, 2016, in connection with International Patent Application No. PCT/JP2015/080969, 7 pgs.

*Primary Examiner* — Luther Behringer
(74) *Attorney, Agent, or Firm* — Chiesa, Shahinian & Giantomasi PC

(57) ABSTRACT

A controller included in a blood flow measurement apparatus controls a scanner to iteratively scan one or more cross sections of an interested blood vessel. An image forming unit forms a phase image that represents chronological change in phase difference in the one or more cross sections based on data acquired through iterative scan. An image processor outputs a predetermined signal based on the chronological change in phase difference represented by the phase image. Upon receiving the predetermined signal, the controller controls the scanner to start scan for acquiring blood flow information on the interested blood vessel.

7 Claims, 11 Drawing Sheets

(51) Int. Cl.
    *A61B 3/117*     (2006.01)
    *A61B 3/14*     (2006.01)

(56) References Cited

U.S. PATENT DOCUMENTS

2015/0313466 A1    11/2015    Yoshida
2016/0302738 A1    10/2016    Yoshida et al.
2016/0310024 A1    10/2016    Yoshida et al.

FOREIGN PATENT DOCUMENTS

JP    2013-184018 A    9/2013
JP    2013-202298 A    10/2013

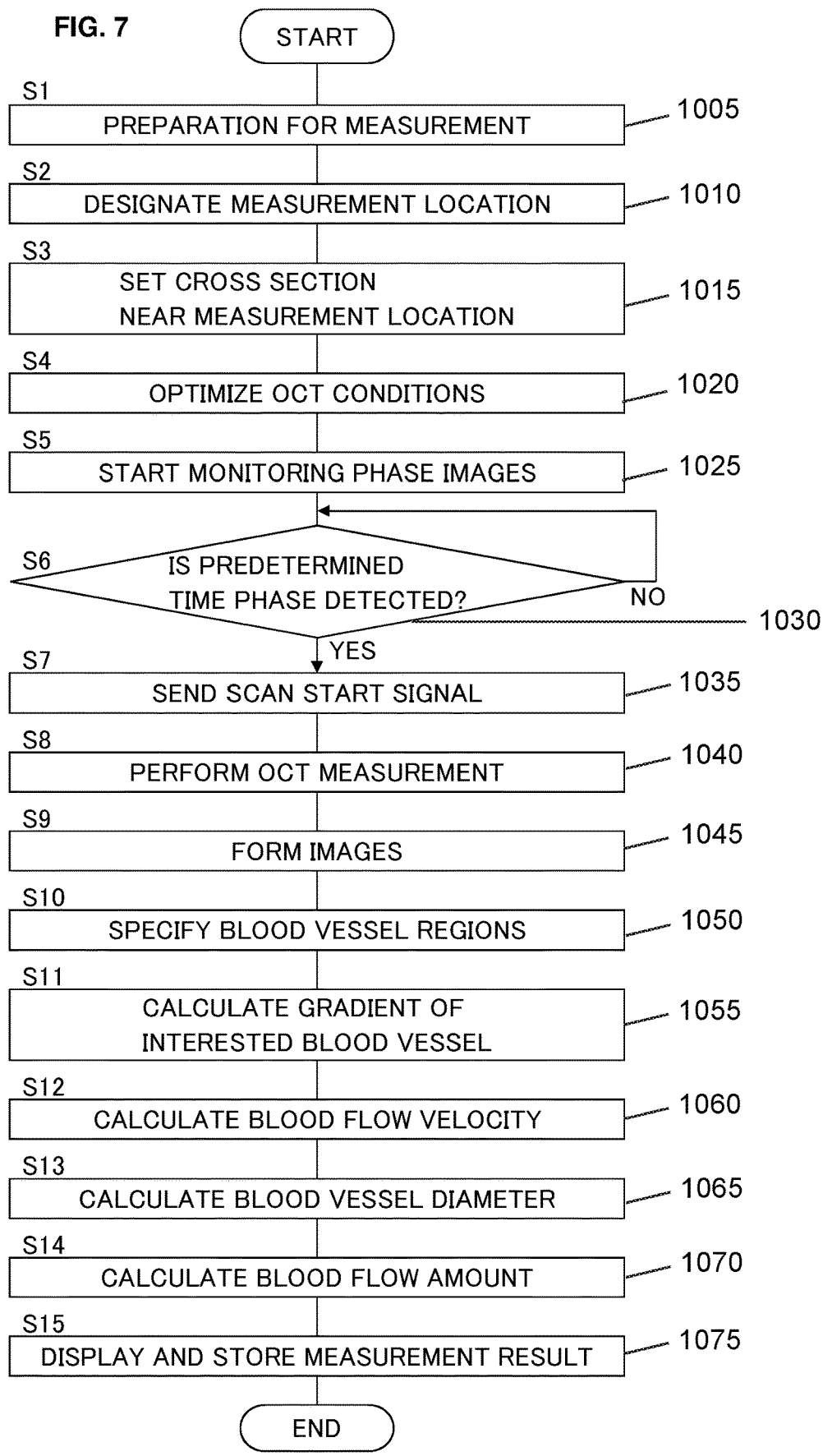

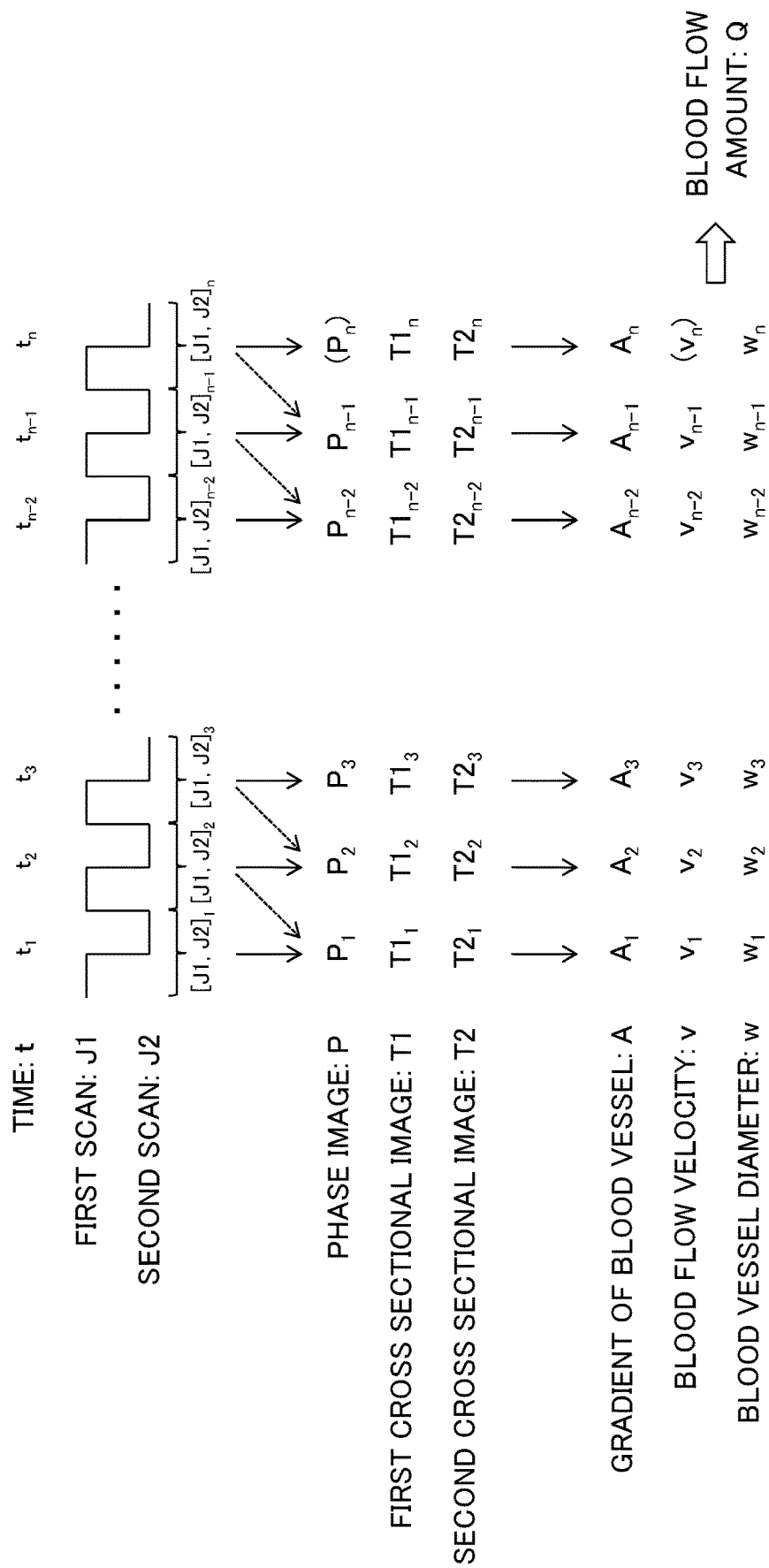

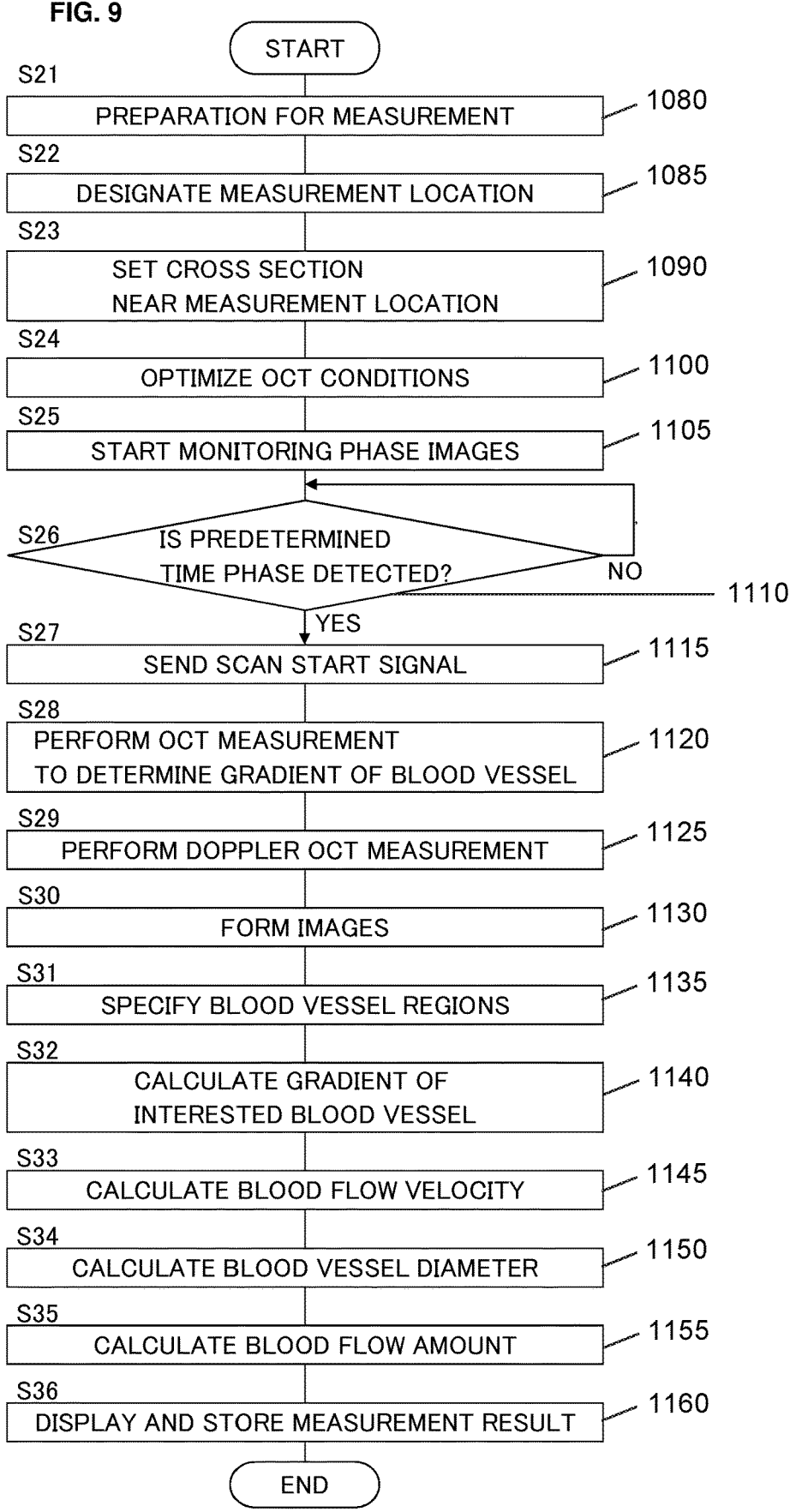

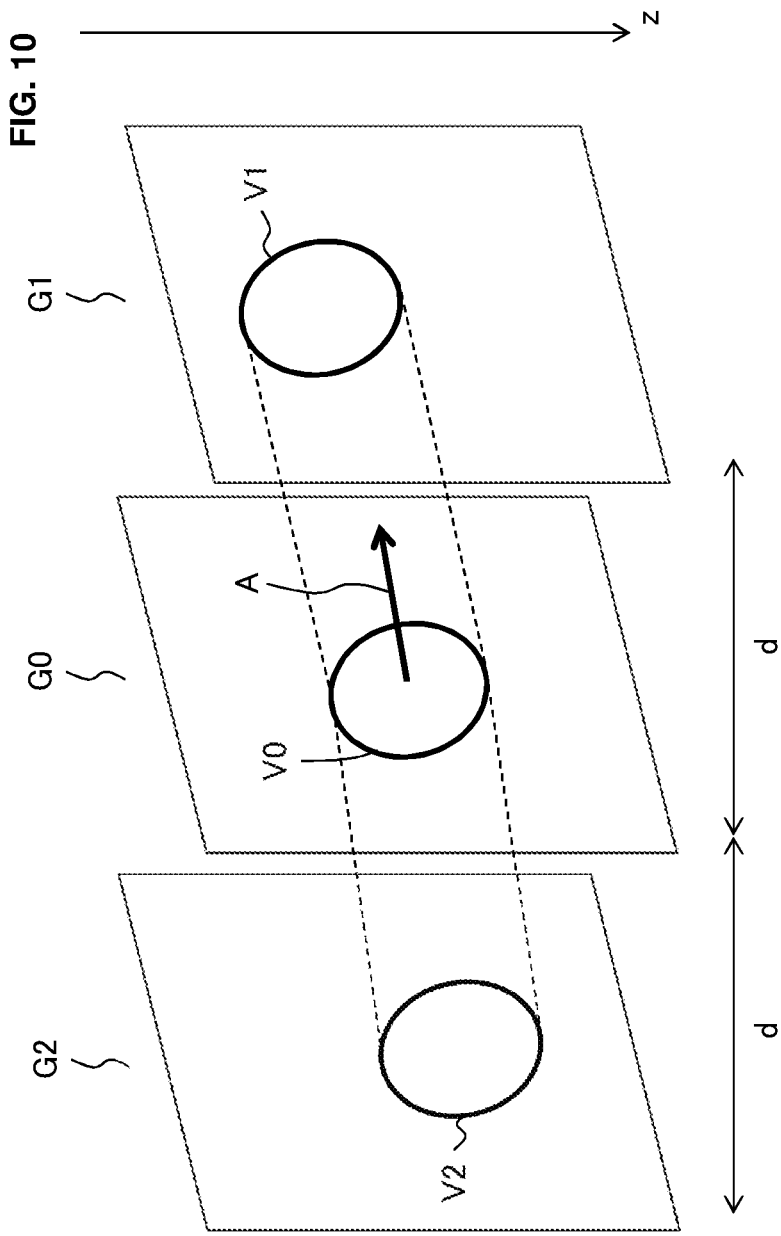

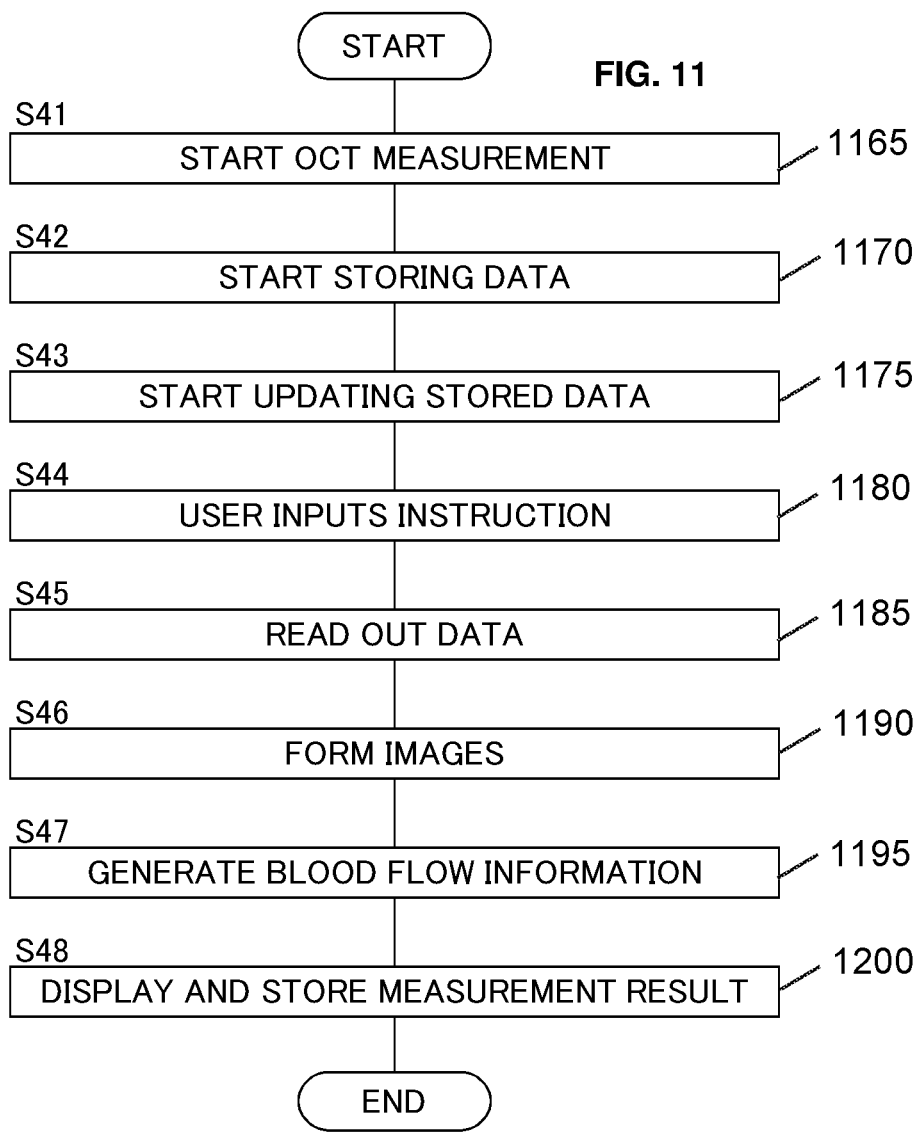

BLOOD FLOW MEASUREMENT APPARATUS

CROSS-REFERENCE TO RELATED APPLICATIONS

This application is a Continuation of prior U.S. patent application Ser. No. 15/536,461, filed Jun. 15, 2017, which is a national stage (under 35 U.S.C. 371) of International Patent Application No. PCT/JP2015/080969, filed Nov. 2, 2015, claiming priority to Japanese Patent Application No. 2014-257033, filed Dec. 19, 2014, all of which are herein incorporated by reference in their entirety.

TECHNICAL FIELD

Embodiments described herein relate generally to a blood flow measurement apparatus.

BACKGROUND

Optical coherence tomography (OCT) is utilized not only for morphology measurement of an object but also for function measurement. For example, OCT apparatuses for blood flow measurement of living bodies are known. The blood flow measurement using OCT is applied to blood vessels of the eye fundus.

SUMMARY

In general, blood flow measurement is carried out during a period equal to or longer than one heartbeat (i.e., one pulsation cycle, or cardiac cycle) to acquire data at various cardiac (time) phases. In addition, the acquisition of the blood flow information using OCT requires the estimation of the orientation of the blood vessel to be measured (referred to as interested blood vessel). This is because the blood flow information is determined based on the Doppler frequency shift that varies according to the angle between the blood flow direction (i.e., the orientation of the blood vessel) and the incident direction of the measurement light on the living body. According to conventional blood flow measurement techniques, the blood flow information is acquired by individually performing the measurement for estimating the blood vessel orientation and Doppler OCT, by applying Doppler OCT to two cross sections, or the like.

In a conventional measurement technique of estimating the orientation of the blood vessel, OCT measurement of the cross section near the interested blood vessel is performed a plurality of times, data having a sufficient signal intensity (i.e., data acquired at a cardiac phase at which a sufficient signal intensity is achieved) is selected from among the plurality of data acquired therefrom, and the orientation of the blood vessel is estimated based on the data selected.

To satisfy such a condition, conventional blood flow measurement techniques perform both: Doppler OCT during a period (e.g., 2 seconds) that has been set so as to securely include a period equal to or longer than one cardiac cycle; and a plurality of measurements for estimating the orientation of the blood vessel. Such conventional techniques have a disadvantage of prolonging measurement time.

The purpose of embodiments is to shorten time taken to perform blood flow measurement.

A blood flow measurement apparatus of an embodiment is configured for acquiring blood flow information on an interested blood vessel of a living body, and includes the followings: a scanner configured to scan a cross section that intersects the interested blood vessel using optical coherence tomography; an image forming unit configured to form an image of the cross section based on data acquired by the scanner; an image processor configured to process the image; and a controller. The controller controls the scanner to iteratively scan one or more cross sections of the interested blood vessel. The image forming unit forms a phase image that represents chronological change in phase difference in the one or more cross sections based on data acquired through iterative scan. The image processor outputs a predetermined signal based on the chronological change in phase difference represented by the phase image. Upon receiving the predetermined signal, the controller controls the scanner to start scan for acquiring the blood flow information.

According to the embodiment, time taken to perform blood flow measurement can be shortened.

BRIEF DESCRIPTION OF THE DRAWINGS

FIG. 7 is a flow chart illustrating an example of the operation of the blood flow measurement apparatus according to the embodiment.

FIG. 8 is a schematic diagram illustrating an example of the operation of the blood flow measurement apparatus according to the embodiment.

FIG. 9 is a flow chart illustrating an example of the operation of the blood flow measurement apparatus according to the embodiment.

FIG. 10 is a schematic diagram illustrating an example of the operation of the blood flow measurement apparatus according to the embodiment.

FIG. 11 is a flow chart illustrating an example of the operation of the blood flow measurement apparatus according to the embodiment.

DETAILED DESCRIPTION

Figure 1:
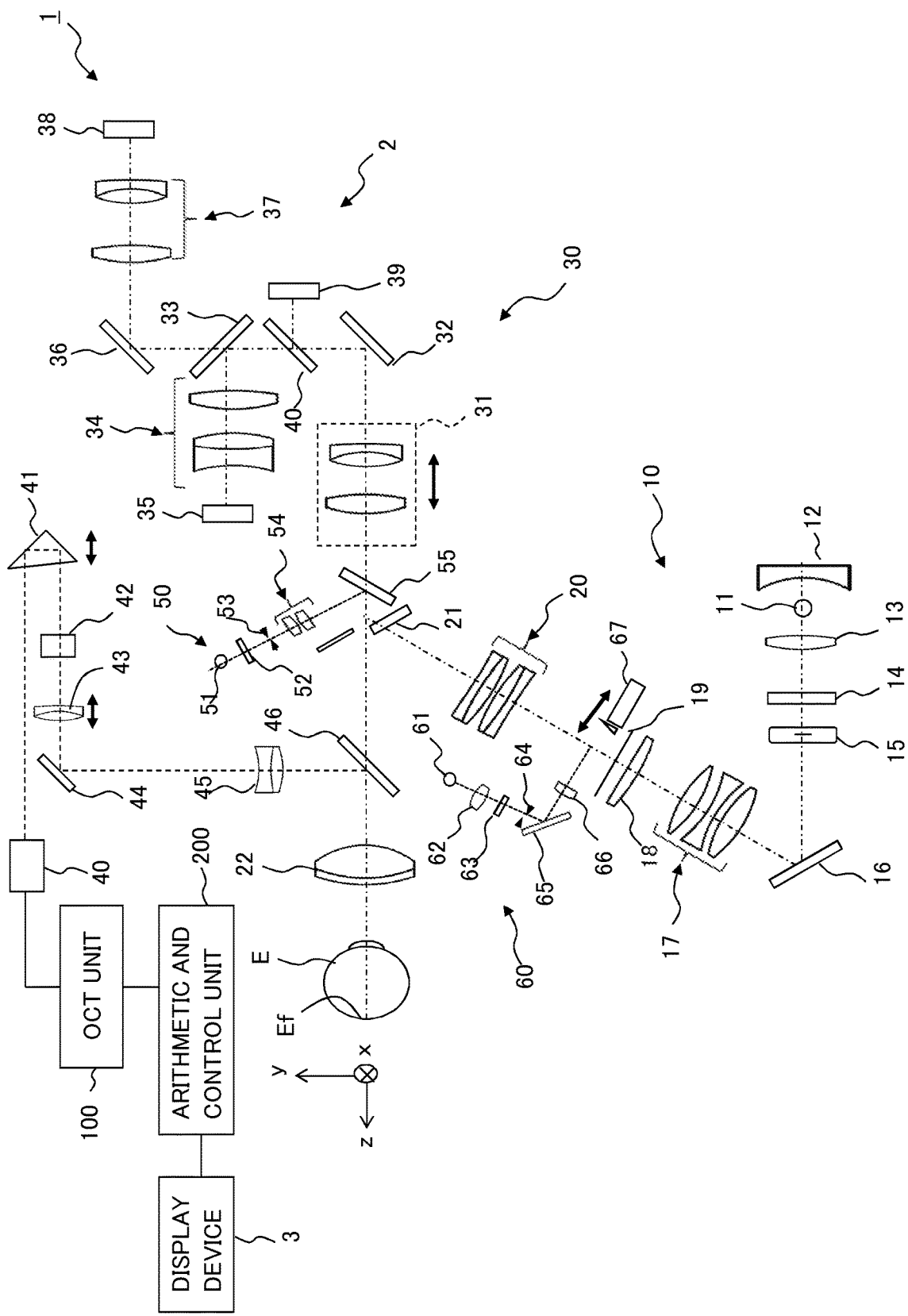
FIG. 1 is a schematic diagram illustrating an example of the configuration of the blood flow measurement apparatus according to the embodiment.

Exemplary embodiments of the present invention will be described in detail with referring to the drawings. Any of the contents of the documents cited in the present specification may be applied to the embodiments below.

A blood flow measurement apparatus of an embodiment acquires information on the blood flow of a living body using OCT. The blood flow measurement apparatus is capable of acquiring images of the living body using OCT. Described below is the case in which Fourier domain OCT (in particular, spectral domain OCT) is utilized to perform the blood flow measurement for eye fundus. The object of blood flow measurement is not necessarily eye fundus. The object of blood flow measurement may be any biological tissue such as skin or internal organs. The type of OCT is not limited to spectral domain OCT. Any type of OCT such as swept source OCT or time domain OCT may be utilized. The embodiment below describes an apparatus that is a combination of an OCT apparatus and a fundus camera. Similar configurations to the embodiment below may be applied to other type such as an apparatus configured as a combination of an OCT apparatus and a slitlamp microscope, or a combination of an OCT apparatus and an ophthalmic operational microscope. Similar configurations to the embodiment below may also be applied to an apparatus having the OCT function only.

First Embodiment

<Configuration>
As shown in FIG. 1, the blood flow measurement apparatus 1 includes the fundus camera unit 2, the OCT unit 100, and the arithmetic and control unit 200. The fundus camera unit 2 has a configuration for photographing the fundus Ef. The OCT unit 100 has a configuration for acquiring OCT images of the fundus Ef. The arithmetic and control unit 200 has a configuration for executing various kinds of calculation and control.

<Fundus Camera Unit>
The fundus camera unit 2 acquires two dimensional images rendering the surface morphology of the fundus Ef (referred to as fundus images). The kinds of the fundus images include observation images and photographed images. An observation image is a monochrome image acquired at a preset frame rate using near infrared light. The kinds of the photographed images include: color images captured using visible flash light; monochrome images captured using near infrared light or visible light (e.g., fluorescence images such as fluorescein angiograms, indocyanine green angiograms, autofluorescence images).

The fundus camera unit 2 includes the illumination optical system 10 and the photographing optical system 30. The illumination optical system 10 irradiates the eye E with illumination light. The photographing optical system 30 receives return light (e.g., fundus reflection light, cornea reflection light, fluorescence, etc.) of the illumination light from the eye E. The fundus camera unit 2 guides measurement light from the OCT unit 100 toward the eye E, and guides return light of the measurement light from the eye E to the OCT unit 100.

Light emitted from the observation light source 11 in the illumination optical system 10 (i.e., observation illumination light) is reflected by the reflection mirror 12 having the curved reflective surface, is refracted by the condenser lens 13, and passes through the visible light cut filter 14. Thereby, the observation illumination light becomes near infrared light. Then, the observation illumination light once converges at a point near the photographing light source 15, is reflected by the mirror 16, passes through the relay lenses 17 and 18, the diaphragm 19, and relay lens 20, is reflected by the peripheral area (that is, the area surrounding the aperture) of the aperture mirror 21, passes through the dichroic mirror 46, is refracted by the objective lens 22, and is projected onto the eye E.

Return light of the observation illumination light from the eye E is refracted by the objective lens 22, passes through the dichroic mirror 46, passes through the aperture formed in the central area of the aperture mirror 21, passes through the dichroic mirror 55, passes through the focusing lens 31, is reflected by the mirror 32, passes through the half mirror 40, is reflected by the dichroic mirror 33, and converges on the light receiving surface of the area sensor 35 with the condenser lens 34. The area sensor 35 detects the return light at a preset frame rate. With this, an observation image of the fundus Ef, an observation image of the anterior segment or the like, is acquired.

Light emitted from the photographing light source 15 (i.e., photographing illumination light) is guided along the same route as that of the observation illumination light, and projected onto the eye E (that is, onto the fundus Ef). Return light (e.g., fundus reflection light, fluorescence, etc.) of the photographing illumination light is also guided along the same route as that of the observation illumination light until the dichroic mirror 33, passes through the dichroic mirror 33, is reflected by the mirror 36, and converges on the light receiving surface of the area sensor 38 with the condenser lens 37. With this, a photographed image of the fundus Ef or the like is acquired.

Liquid crystal display (LCD) 39 displays a fixation target, an optotype (visual acuity chart), and the like. Part of light output from the LCD 39 is reflected by the half mirror 40, is reflected by the mirror 32, passes through the focusing lens 31 and the dichroic mirror 55, passes through the aperture of the aperture mirror 21, passes through the dichroic mirror 46, is refracted by the objective lens 22, and is projected onto the eye (that is, onto the fundus Ef). The fixation position of the eye E is changed by changing the displayed position of the fixation target on the LCD 39.

The fundus camera unit 2 includes the alignment optical system 50 and the focus optical system 60. The alignment optical system 50 generates an indicator for position adjustment of the optical system of the apparatus with respect to the eye E. Such position adjustment is referred to as alignment, and the indicator for the alignment is referred to as the alignment indicator. The focus optical system 60 generates an indicator for focus adjustment with respect to the eye E. The indicator for the focus adjustment is referred to as the split indicator.

Near infrared light emitted from the light emitting diode (LED) 51 in the alignment optical system 50 (referred to as alignment light) passes through the diaphragms 52 and 53 and the relay lens 54, is reflected by the dichroic mirror 55, passes through the aperture of the aperture mirror 21, passes through the dichroic mirror 46, and is projected onto the eye E (i.e., the cornea) with the objective lens 22. Return light of the alignment light is guided along the same route as that of the return light of the observation illumination light, and detected by the area sensor 35. The image detected by the area sensor 35 (referred to as an alignment indicator image) is rendered in the observation image. The user or the arithmetic and control unit 200 can perform alignment based on the position of the alignment indicator image in the same manner as with conventional fundus cameras.

When performing focus adjustment, the reflective surface of the reflection rod 67 is placed in the optical path of the illumination optical system 10 in an inclined manner. Near infrared light emitted from the LED 61 in the focus optical system 60 (referred to as focus light) passes through the relay lens 62, is split into two light beams with the split indicator plate 63, passes through the two-aperture diaphragm 64, is reflected by the mirror 65, once converges on the reflective surface of the reflection rod 67 with the condenser lens 66, is reflected by the reflection rod 67, passes through the relay lens 20, is reflected by the aperture mirror 21, passes through the dichroic mirror 46, is refracted by the objective lens 22, and is projected onto the eye E (i.e., the fundus Ef). Return light of the focus light is guided along the same route as that of the return light of the alignment light, and detected by the area sensor 35. The image detected by the area sensor 35 (referred to as a split indicator image) is rendered in the observation image. The user or the arithmetic and control unit 200 can perform focus adjustment by moving the focusing lens 31 and the focus optical system 60 based on the position of the split indicator image in the same manner as with conventional fundus cameras. The focus driver 31A shown in FIG. 3 moves the focusing lens 31, and a driver mechanism (not illustrated) moves the focus optical system 60.

After the completion of alignment (and focus adjustment), tracking may be performed. Tracking is an operation for moving the optical system of the apparatus in accordance with the movement of the eye E.

The dichroic mirror 46 couples the optical path for fundus photography and the optical path for OCT together. The optical path for OCT is referred to as a measurement arm, sample arm, or the like. The dichroic mirror is designed to reflect light of wavelength bands for OCT and to transmit light for fundus photography. Listed from the OCT unit 100 side, the collimator lens unit 40, the optical path length (OPL) changer 41, the optical scanner 42, the focusing lens 43, the mirror 44, and the relay lens 45 are placed in the optical path for OCT.

The optical path length changer 41 changes the length of the measurement arm. The optical path length changer 41 includes, for example, a corner cube movable in the direction shown by the arrow in the FIG. 1. Change of the optical path length of the measurement arm may be utilized for the adjustment of the optical path length according to the axial length of the eye E, the adjustment of the interference state, or the like.

The optical scanner 42 has a configuration capable of two-dimensionally deflecting light guided along the measurement arm (i.e., the measurement light LS). In an example, the optical scanner 42 is configured to be capable of deflecting the measurement light LS in mutually orthogonal directions (e.g., the x direction and the y direction). With such a configuration, various types of scan patterns can be realized. When a configuration for anterior segment OCT (e.g., an attachment including a lens system) is employed, the anterior segment of the eye E is scanned with the measurement light LS. The optical scanner 42 includes, for example, a Galvano mirror, micro electro mechanical systems (MEMS) mirror, resonant mirror, or the like.

<OCT Unit>

Figure 2:
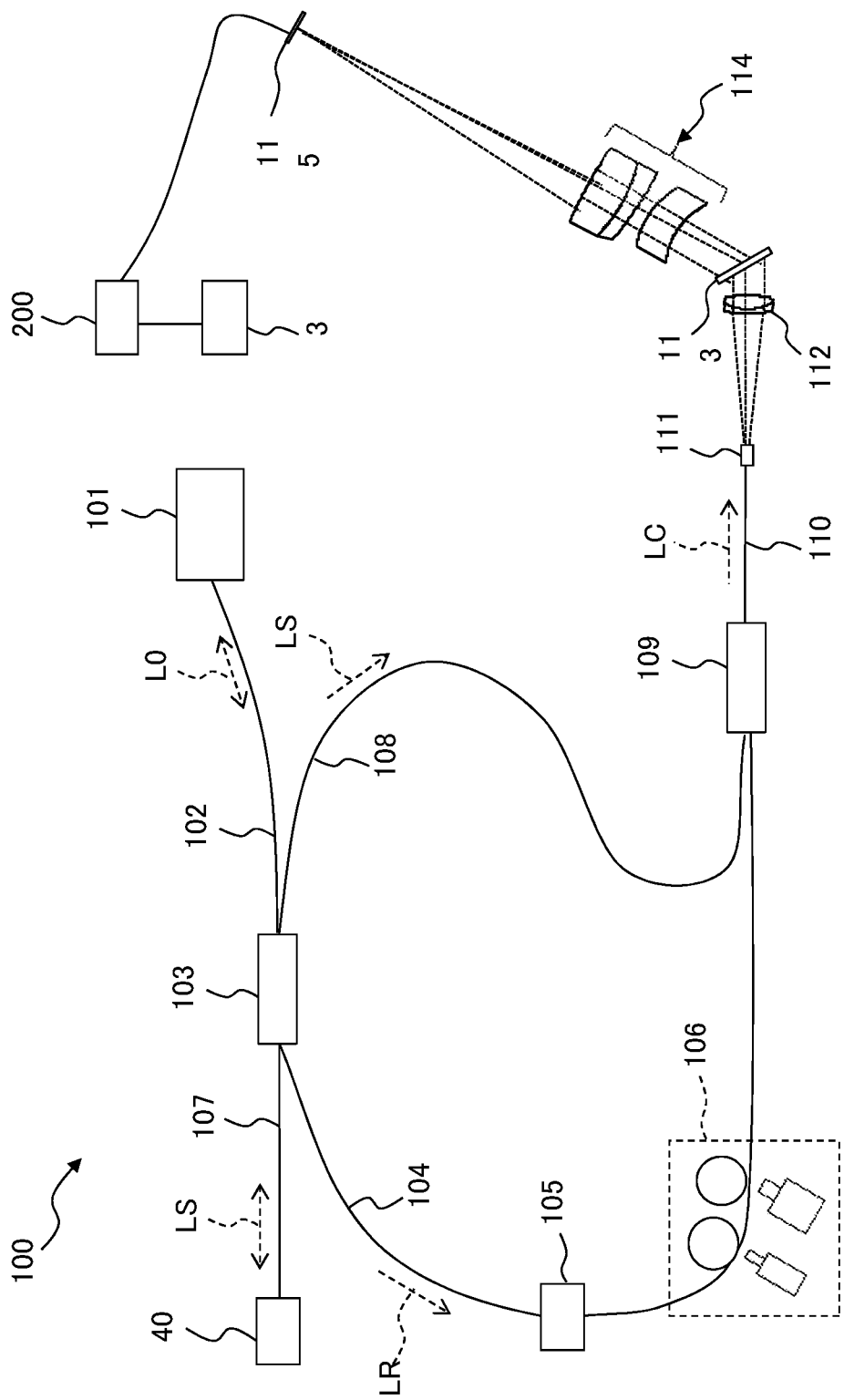
FIG. 2 is a schematic diagram illustrating an example of the configuration of the blood flow measurement apparatus according to the embodiment.

FIG. 2 shows a configuration example of the OCT unit 100. The configuration of the OCT unit 100 depends on the type of OCT applied. The configuration shown in FIG. 2 is an example for spectral domain OCT. The spectral domain OCT system, in general, includes a low coherence light source and a spectrometer. On the other hand, the swept source OCT system includes, for example, a wavelength tunable light source and a balanced photo diode.

In the spectral domain OCT system, the light L0 emitted from the light source unit 101 is broadband, low coherence light. In an example, the light L0 may include near infrared wavelength bands (e.g., about 800 nm to 900 nm), and the temporal coherence length of the light L0 may be about several tens μm. Alternatively, the light L0 may be near infrared light having the central wavelength of about 1040 nm to 1060 nm. The light source unit 101 includes a light emitting device such as a super luminescent diode (SLD), an LED, or a semiconductor optical amplifier (SOA).

The light L0 output from the light source unit 101 is guided to the fiber coupler 103 through the optical fiber 102, and is split into the measurement light LS and the reference light LR.

The reference light LR is guided to the optical attenuator 105 through the optical fiber 104. Under the control of the arithmetic and control unit 200, the optical attenuator 105 automatically adjusts the amount of the reference light LR guided through the optical fiber 104 as with conventional techniques. The reference light LR, the amount of which has been adjusted by the optical attenuator 105, is guided to the polarization controller 106 through the optical fiber 104. Under the control of the arithmetic and control unit 200, the polarization controller 106 controls the polarization state of the reference light LR guided through the optical fiber 104 as with conventional techniques. The reference light LR, the polarization state of which has been adjusted, is guided to the fiber coupler 109.

The measurement light LS generated by the fiber coupler 103 is guided through the optical fiber 107, and is converted to a parallel light beam with the collimator lens unit 40. Then, the measurement light LS passes through the optical path length changer 41, the optical scanner 42, the focusing lens 43, the mirror 44, and the relay lens 45, is reflected by the dichroic mirror 46, is refracted by the objective lens 22, and is projected onto the eye E (that is, onto the fundus Ef). The measurement light LS is scattered and reflected at various depth positions of the fundus Ef. Return light of the measurement light LS (e.g., backscattering light, reflection light, fluorescence) travels along the same route as the outward way in the opposite direction, is guided to the fiber coupler 103, and is guided to the fiber coupler 109 through the optical fiber 108. The focusing lens 43 is moved by a focus driver (not illustrated).

The fiber coupler 109 superposes the return light of the measurement light LS and the reference light LR that has traveled through the optical fiber 104. Interference light LC thus generated is guided through the optical fiber 110, exits from the exit end 111 of the optical fiber 110, is converted to a parallel light beam with the collimator lens 112, is split into spectra with the diffraction grating 113, converges with the condenser lens 114, and is projected on the light receiving surface of the optical detector 115. The optical detector 115 is, for example, a line sensor, and detects the respective spectral components of the interference light LC split into spectra and generates an electric signal (that is, a detection signal). The detection signal generated is sent to the arithmetic and control unit 200.

<Arithmetic and Control Unit>

The arithmetic and control unit 200 executes control of the fundus camera 2, the display device 3, and the OCT unit 100, various kinds of calculation processing, formation of OCT images, etc. The arithmetic and control unit 200 includes a user interface such as a display device, an input device, an operation device. The description of the configuration of the arithmetic and control unit 200 will be given in the description of the control system below.

<Control System>

Figure 3:
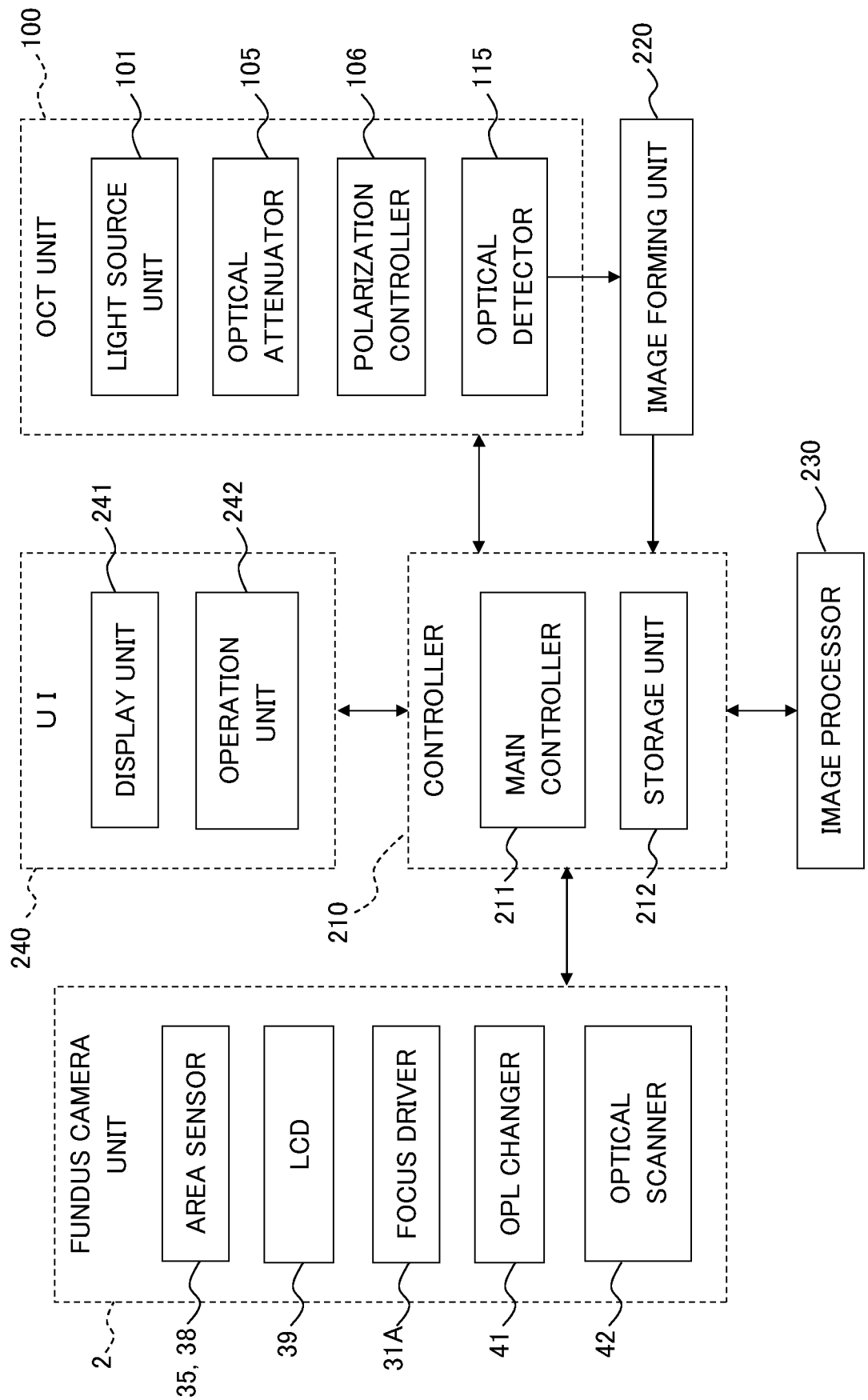
FIG. 3 is a schematic diagram illustrating an example of the configuration of the blood flow measurement apparatus according to the embodiment.
Figure 4:
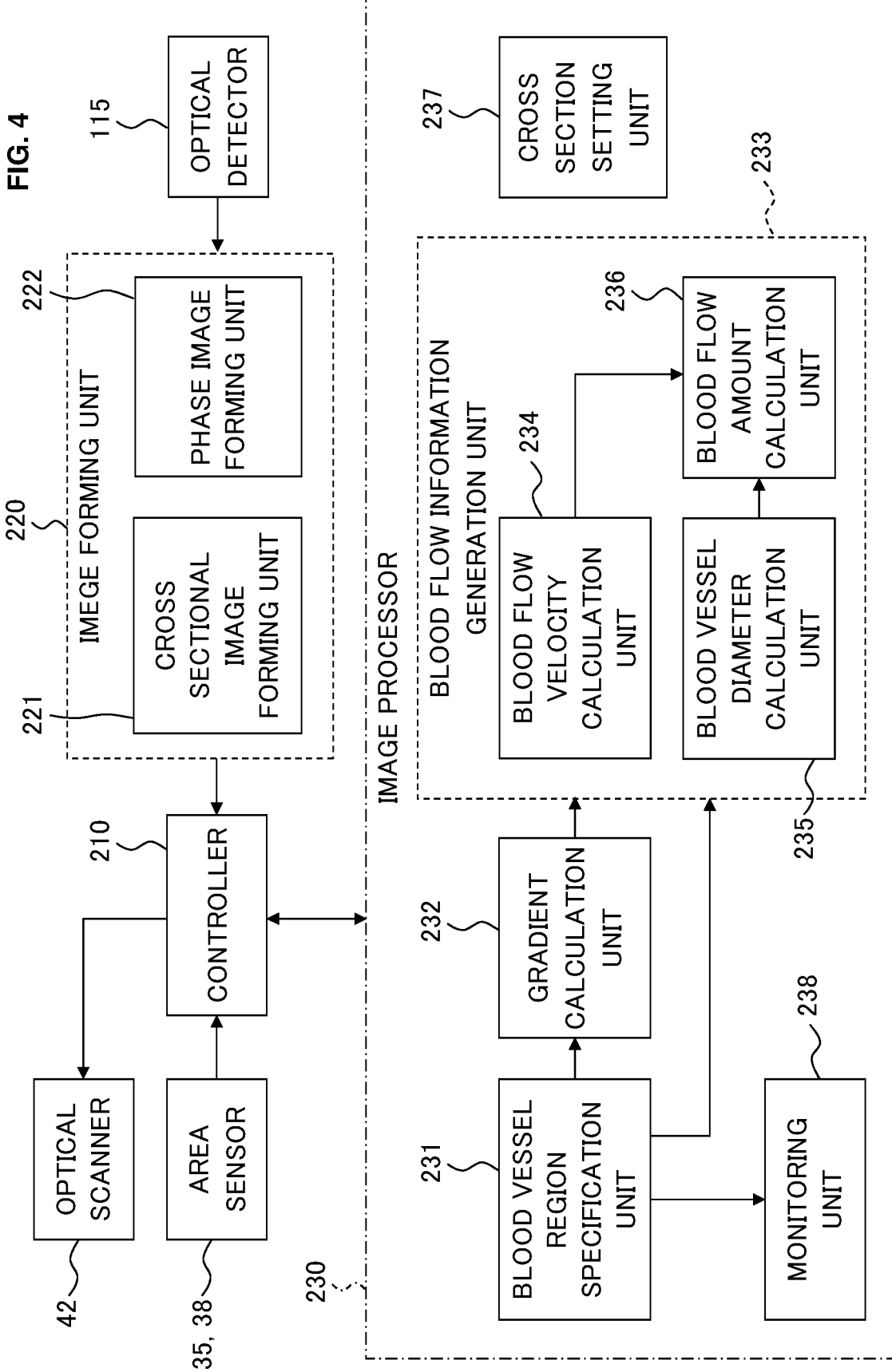
FIG. 4 is a schematic diagram illustrating an example of the configuration of the blood flow measurement apparatus according to the embodiment.

The control system of the blood flow measurement apparatus 1 will be described with referring to FIGS. 3 and 4.

(Controller)

The controller 210 is the center of the control system of the blood flow measurement apparatus 1. The controller 210 includes the main controller 211 and the storage unit 212.

(Main Controller)

The main controller 211 executes control of the fundus camera 2, the OCT unit 100, and the arithmetic and control unit 200. The main controller 211 stores data in the storage unit 212 and reads out data from the storage unit 212.

(Storage Unit)

The storage unit 212 stores various kinds of data. Examples of data stored in the storage unit 212 include, for example, OCT images, fundus images, and subject's eye information. The subject's eye information is information on subject's eyes and/or subjects, and includes input information such as patient IDs, medical information such as electronic medical records, or the like. The storage unit 212 stores computer programs and data for operating the blood flow measurement apparatus 1.

(Image Forming Unit)

The image forming unit 220 forms image data of a cross sectional image and image data of a phase image based on detection signals from the optical detector 115. The image data will be described later. Sometimes, the present specification does not make distinction between "image data" and an "image" created based on the image data. The image forming unit 220 includes the cross sectional image forming unit 221 and the phase image forming unit 222.

Figure 5:
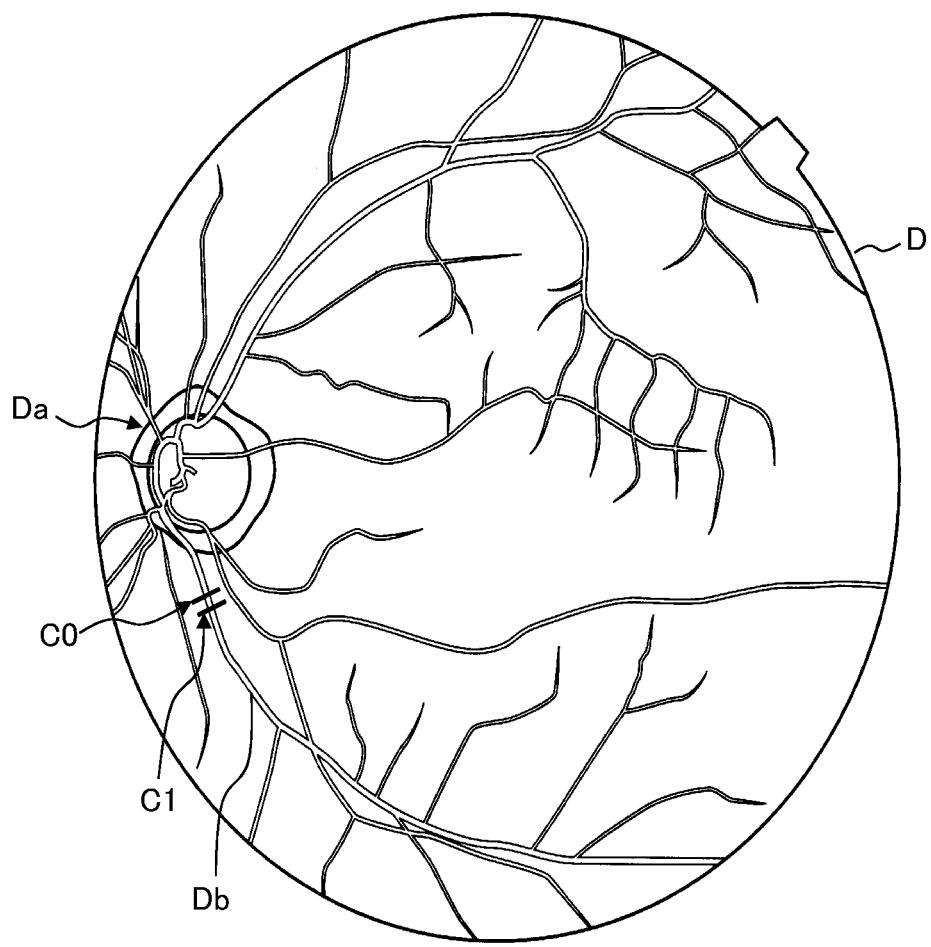
FIG. 5 is a schematic diagram illustrating an example of the operation of the blood flow measurement apparatus according to the embodiment.

In the present embodiment, two different kinds of scans (first scan and second scan) are applied to the fundus Ef. In the first scan, a first cross section that intersects a predetermined interested blood vessel of the fundus Ef is repeatedly scanned with the measurement light LS. In the second scan, a second cross section that intersects the interested blood vessel is scanned with the measurement light LS. The second cross section is set near the first cross section. It may be desirable that the first cross section and the second cross section are oriented in such a manner that they are orthogonal to the running direction of the interested blood vessel. FIG. 5 shows a specific example of the first cross section and the second cross section. On the fundus image D shown in FIG. 5, the first cross section C0 and the second cross section C1 are illustrated. The first cross section C0 and the second cross section C1 are set near the optic nerve head Da of the fundus Ef. The first cross section C0 and the second cross section C1 are set in such a manner that both of them intersect the predetermined interested blood vessel db. The second cross section C1 may be set more on upstream side of the interested blood vessel db than the first cross section C0, or may be set more on downstream side. The second cross section may include two or more cross sections.

It may be desirable that the first scan and the second scan are performed during a period equal to or longer than one heartbeat (i.e., one pulsation cycle, or cardiac cycle) of the heart of the patient. With this, blood flow information is acquired for all time phases of the cardiac cycle. The execution period of the first scan may be a preset period with a constant length, or may be individually set for each patient or each examination. In the former case, a period shorter than conventional execution period is set. For example, in the conventional execution, a period sufficiently longer than the cardiac cycle is applied (e.g., 2 seconds). On the other hand, in the present embodiment, a period of the cardiac cycle (e.g., 1 second) or a slightly longer period than the same can be applied. The latter case is executed with referring to examination data such as an electro cardiogram of the patient. Any factors other than the cardiac cycle may be considered. Examples of the factors include examination time (i.e., burden on the patient), response time of the optical scanner 42 (i.e., scan intervals), and response time of the optical detector 115 (i.e., scan intervals).

(Cross Sectional Image Forming Unit)

The cross sectional image forming unit 221 forms a cross sectional image (referred to as a first cross sectional image) that represents chronological change in morphology in the first cross section based on detection results of the interference light LC acquired through the first scan. This image formation will be described more in detail. As mentioned above, the first scan is iterative scan of the first cross section C0. During the first scan, detection signals are successively input from the optical detector 115 of the OCT unit 100 to the cross sectional image forming unit 221. Based on detection signals corresponding to each single scan of the first cross section C0, the cross sectional image forming unit 221 forms a single cross sectional image in the first cross section C0. The cross sectional image forming unit 221 iterates such image formation as many times as the number of repetition of the first scan. Thereby, the cross sectional image forming unit 221 forms a series of cross sectional images arranged in time series order. The cross sectional image forming unit 221 may divide these cross sectional images into a plurality of groups and synthesize (e.g., average) cross sectional images in each group to improve image quality.

The cross sectional image forming unit 221 forms a cross sectional image (referred to as a second cross sectional image) that represents morphology in the second cross section C1 based on detection results of the interference light LC acquired through the second scan of the second cross section C1. This image formation is executed in the same manner as for the first cross sectional image. The second cross sectional image may be a single cross sectional image while the first cross sectional image is a series of cross sectional images arranged in time series order. The image quality of the second cross sectional image may be improved by scanning the second cross section C1 a plurality of times and by synthesizing (e.g., averaging) resulting cross sectional images.

Processing of forming such cross sectional images includes noise elimination (noise reduction), filtering, fast Fourier transform (FFT), and the like as in conventional spectral domain OCT techniques. When other type of OCT is applied, the cross sectional image forming unit 221 executes known processing according to the type of OCT.

(Phase Image Forming Unit)

The phase image forming unit 222 forms a phase image that represents chronological change in phase difference in the first cross section based on detection results of the interference light LC acquired through the first scan. The detection results processed here is the same as that processed in the formation of the first cross sectional image performed by the cross sectional image forming unit 221. Accordingly, position matching between the first cross sectional image and the phase image can be performed. That is, pixels in the first cross sectional image and those in the phase image can be associated with each other in a natural manner.

An example of the method of the formation of phase images will be described. A phase image in this example is obtained by calculating the phase differences between adjacent A-line complex signals (that is, signals corresponding to adjacent scan points). In other words, a phase image in this example is formed based on chronological change in the pixel value (brightness value) of each pixel in the first cross sectional image. For any pixel, the phase image forming unit 222 creates a graph of the chronological change in the brightness value of the concerned pixel. The phase image forming unit 222 determines the phase difference $\Delta\varphi$ between two time points t1 and t2 that are apart from each other by a preset time interval $\Delta t$ in the graph. Here, $t2=t1+\Delta t$. The phase difference $\Delta\varphi$ is defined as the phase difference $\Delta\varphi(t1)$ at the time point t1. More generally, the phase difference Δφ may be defined as the phase difference at any time point between t1 and t2 (including t1 and t2). By executing such processing for each of a plurality of time points set in advance, the chronological change in the phase difference at the concerning pixel.

A phase image is formed by representing, as an image, the values of the phase differences at the respective time points for the respective pixels. Such imaging processing can be realized by representing the values of the phase differences with colors. It is possible to assign different colors to a case where phase increases with the lapse of time and a case where it decreases. For example, red is assigned to the former case while blue is assigned to the latter case. It is also possible to represent the magnitude of the amount of change in phase with the density of display color. With such representation methods, the direction and/or magnitude of blood flow can be clearly represented with colors. The processing described here is applied to each pixel. Thereby, a phase image is formed.

The time interval Δt is set sufficiently small to secure phase correlation. This allows to obtain the chronological change in phase difference. Here, oversampling is executed in which the time interval Δt is set to be a value smaller than the period corresponding to the resolution of cross sectional images in the scan with the measurement light LS.

<Image Processor>

The image processor 230 applies various kinds of image processing, analysis, or the like to images formed by the image forming unit 220. For example, the image processor 230 executes various kinds of image correction such as brightness correction or dispersion correction. In addition, the image processor 230 applies various kinds of image processing, analysis, or the like to images (e.g., fundus images, anterior eye images) acquired by the fundus camera unit 2.

The image processor 230 includes the blood vessel region specification unit 231, the gradient calculation unit 232, and the blood flow information generation unit 233. The blood flow information generation unit 233 includes the blood flow velocity calculation unit 234, the blood vessel diameter calculation unit 235, and the blood flow amount calculation unit 236. In addition, the image processor 230 includes the cross section setting unit 237 and the monitoring unit 238. These units 231 to 238 will be described below.

<Blood Vessel Region Specification Unit>

The blood vessel region specification unit 231 specifies a blood vessel region corresponding to the interested blood vessel db for each of the first cross sectional image, the second cross sectional image, and the phase image. The specification can be executed by analyzing the pixel value of each pixel. This analysis may be thresholding.

Although the first cross sectional image and the second cross sectional image have enough resolution to apply the analysis, the phase image may not have enough resolution to specify the boundary (i.e., contour) of the blood vessel region. However, since the phase image is used for the generation of blood flow information, the blood vessel region in the phase image must be specified with high precision and high accuracy. On that account, the following processing can be employed to specify the blood vessel region in the phase image with higher accuracy.

As described above, the first cross sectional image and the phase image are formed based on the common detection signals, and the pixels of the first cross sectional image and those of the phase image can be associated in a natural manner. With this association, the blood vessel region specification unit 231 first analyzes the first cross sectional image to determine the blood vessel region in the first cross sectional image, and then determines the image region in the phase image consisting of the pixels corresponding to the pixels included in the blood vessel region in the first cross sectional image. The image region determined is regarded as the blood vessel region in the phase image. With such processing, the blood vessel region in the phase image can be specified with high precision and high accuracy.

<Gradient Calculation Unit>

Based on the distance between the first cross section and the second cross section (referred to as cross section interval) and the result of the specification of the blood vessel regions, the gradient calculation unit 232 calculates the gradient (or, inclination or tilt) of the interested blood vessel db at the first cross section. The cross section interval is set in advance, and an example of which will be described later in the description of the cross section setting unit 237.

The gradient of the interested blood vessel db is calculated for the following reason. The blood flow information is obtained by using Doppler OCT technique. The velocity component of blood flow contributing to Doppler shift is the component in the projection direction of the measurement light LS. Therefore, even when the blood flow velocity is the same, Doppler shift given to the measurement light LS changes according to the angle between the blood flow direction (i.e., the gradient of the interested blood vessel) and the projection direction of the measurement light LS. Thereby, the blood flow information acquired is also changed. In order to avoid such a problem, it is necessary to determine the gradient of the interested blood vessel db and perform the calculation of the blood flow velocity based on the gradient.

Figure 6:
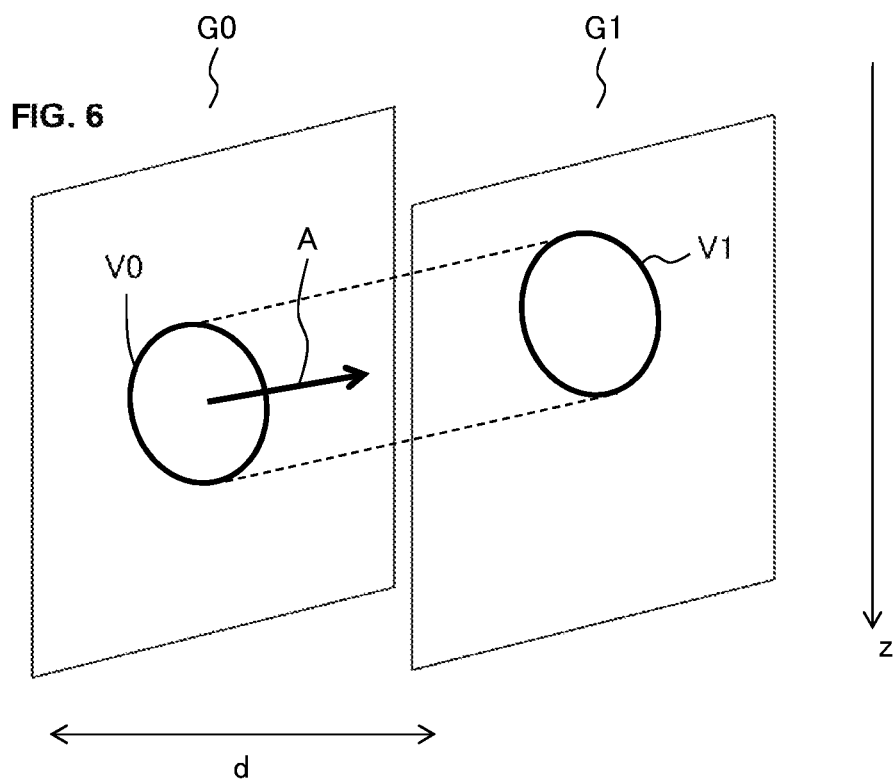
FIG. 6 is a schematic diagram illustrating an example of the operation of the blood flow measurement apparatus according to the embodiment.

A method of calculating the gradient of the interested blood vessel db will be described with referring to FIG. 6. The symbol G0 indicates the first cross sectional image of the first cross section C0, and the symbol G1 indicates the second cross sectional image of the second cross section C1. The symbol V0 indicates the blood vessel region in the first cross sectional image G0, and the symbol V1 indicates the blood vessel region in the second cross sectional image G1. In FIG. 6, the z coordinate axis is oriented downward, and substantially coincides with the projection direction of the measurement light LS. Further, the cross section interval is indicated by "d".

The gradient calculation unit 232 calculates the gradient "A" of the interested blood vessel db at the first cross section C0 based on the positional relationship between the two blood vessel regions V0 and V1. The positional relationship is obtained, for example, by connecting the two blood vessel regions V0 and V1. More specifically, the gradient calculation unit 232 specifies a representative point in the blood vessel region V0 and a representative point in the blood vessel region V1, and connects the two representative points with a line segment. The representative point may be the center position, the position of the center of gravity, the highest position (the position corresponding to the smallest z coordinate value), the lowest position (the position corresponding to the largest z coordinate value), or the like.

Further, the gradient calculation unit 232 calculates the gradient A based on the line segment connecting the two representative points. More specifically, the gradient calculation unit 232 calculates the gradient of the line segment connecting the representative point in the first cross section C0 and the representative point in the second cross section C1, and set the calculated value to be the gradient A. The cross section interval "d" is used, in the calculation of the line segment, to embed the two cross sectional images G0 and G1 in the xyz coordinate system.

In the present example, a single value is obtained for the gradient. However, two or more gradients corresponding to two or more positions in the blood flow region V0 may be obtained. In such a case, the obtained two or more gradient values may be used separately. Alternatively, it is possible to execute statistical calculation to obtain a single value (e.g., mean value) from the obtained two or more gradient values, and set the obtained single value to be the gradient A.

<Blood Flow Information Generation Unit>

The blood flow information generation unit 233 generates blood flow information on the interested blood vessel db based on the phase image and the gradient A of the interested blood vessel db. The following is a description of a configuration example for executing the generation of the blood flow information. As mentioned above, the blood flow information generation unit 233 includes the blood flow velocity calculation unit 234, the blood vessel diameter calculation unit 235, and the blood flow amount calculation unit 236.

(Blood Flow Velocity Calculation Unit)

Based on the phase image (i.e., chronological change in phase difference) and the gradient A of the interested blood vessel db, the blood flow velocity calculation unit 234 calculates the blood flow velocity at the first cross section C0 for the blood flowing through the interested blood vessel db. The parameter to be calculated may be the blood flow velocity at a certain time point, or may be the chronological change in the blood flow velocity. The chronological change in the blood flow velocity is referred to as blood flow velocity variation information. When the blood flow velocity at a certain time point is determined, the blood flow velocity at a predetermined time phase in an electro cardiogram (e.g., time phase corresponding to R wave) may be selectively acquired. When the chronological change in the blood flow velocity is determined, the measurement period is the whole or an arbitrary part of the period taken for the scan of the first cross section C0.

When the blood flow velocity variation information is acquired, the blood flow velocity calculation unit 234 can further calculate a statistic of the blood flow velocity in the measurement period. Examples of the statistic include the mean value, the standard deviation, the variance, the median, the global maximum, the global minimum, the local maximum, and the local minimum. The blood flow velocity calculation unit 234 can also create a histogram on the blood flow velocity values.

The blood flow velocity calculation unit 234 calculates the blood flow velocity using Doppler OCT technique as described above. In the blood flow velocity calculation, the gradient A of the interested blood vessel db at the first cross section C0 calculated by the gradient calculation unit 232 is taken into account. Specifically, the blood flow velocity calculation unit 234 applies the following formula to the blood flow velocity calculation.

$$\Delta f = \frac{2nv\cos\theta}{\lambda} \qquad \text{(Formula 1)}$$

Here:

$\Delta f$ indicates the Doppler shift given to scattered light of the measurement light LS;

n indicates the refractive index of medium;

v indicates the flow velocity of the medium (blood flow velocity);

$\theta$ indicates the angle between projection direction of the measurement light LS and the flow vector of the medium; and $\lambda$ indicates the center wavelength of the measurement light LS.

In the present embodiment, n and $\lambda$ are known, $\Delta f$ is obtained from the chronological change of the phase difference, and $\theta$ is obtained from the gradient A (alternatively, $\theta$ is the gradient A). The blood flow velocity v is calculated by substituting these values into the above formula.

When the chronological changes in the parameters are taken into account, it can be expressed that the Doppler shift $\Delta f=\Delta f(t)$ and the angle $\theta=\theta(t)$. Here, t is a variable representing time. The blood flow velocity calculation unit 234 can use the following formula to determine the blood flow velocity v(t) at an arbitrary time, or to determine the chronological changes in the blood flow velocity v(t).

$$\Delta f(t) = \frac{2nv(t)\cos\theta(t)}{\lambda} \qquad \text{(Formula 2)}$$

(Blood Vessel Diameter Calculation Unit)

The blood vessel diameter calculation unit 235 calculates the diameter of the interested blood vessel db at the first cross section C0. Examples of this calculation include a first calculation method that utilizes a fundus image and a second calculation method that utilizes a cross sectional image.

When applying the first calculation method, an area of the fundus Ef including the location of the first cross section C0 is photographed in advance. The fundus image thus obtained may be an observation image (e.g., a frame(s) thereof), or may be a photographed image. When the photographed image is a color image, any image obtained from the color image (e.g., a red-free image) may be used.

The blood vessel diameter calculation unit 235 sets a scale of the fundus image based on various kinds of factors that determines the relationship between the scale of images and the scale in the real space such as the photographing angle of view (photographing magnification), the working distance, information on eyeball optical system. The scale of the fundus image may represent length in the real space. As a specific example, the scale associates interval between adjacent pixels with the scale in the real space (e.g., pixel interval=10 μm). It is possible to determine, in advance, the relationship between various values of the above factors and the scale in the real space, and store a table or a graph that represents the determined relationship. In this case, the blood vessel diameter calculation unit 235 selects the scale corresponding to the above factors, and uses the selected scale.

Based on the scale and the pixels included in the blood vessel region V0, the blood vessel diameter calculation unit 235 calculates the diameter of the interested blood vessel db at the first cross section C0, that is, the diameter of the blood vessel region V0. As a specific example, the blood vessel diameter calculation unit 235 may calculate the maximum or the mean value of a plurality of diameters of the blood vessel region V0 corresponding to different directions. The blood vessel diameter calculation unit 235 may determine an approximate circle or an approximate ellipse of the contour of the blood vessel region V0, and calculate the diameter of the approximate circle or the approximate ellipse. Note that once the blood vessel diameter of the blood vessel region V0 is determined, the area of the blood vessel region V0 can (substantially) be calculated. That is, it is possible to substantially associate the blood vessel diameter with the area in one-to-one fashion. Hence, the area can be calculated in place of the blood vessel diameter.

The second calculation method will be described. In the second calculation method, a cross sectional image of the fundus Ef at the first cross section C0 is used. The cross sectional image may be the first cross sectional image, the phase image, or any other image.

The scale of the cross sectional image is determined according to the scan mode of the measurement light LS. In the present embodiment, the first cross section C0 is scanned as shown in FIG. 5. The length of the first cross section C0 is determined based on various kinds of factors that define the relationship between the scale of an image and the scale in the real space such as the working distance, the information about eyeball optical system. The blood vessel diameter calculation unit 235, for example, determines the interval between adjacent pixels based on the length of the first cross section C0, and calculates the diameter of the interested blood vessel db at the first cross section C0 in the same manner as in the first calculation method. The chronological change in the blood vessel diameter can also be determined.

(Blood Flow Amount Calculation Unit)

Based on the calculation result of the blood flow velocity and the calculation result of the blood vessel diameter, the blood flow amount calculation unit 236 calculates the flow amount (or, flow volume or flow rate) of the blood that flows through the interested blood vessel db. An example of this processing will be described below.

It is assumed that the blood flow in a blood vessel is the Hagen-Poiseuille flow. The blood vessel diameter is denoted by w, and the maximum blood flow velocity is denoted by Vm. Then, the blood flow amount Q is expressed as in the following formula.

$$Q = \frac{\pi w^2}{8} Vm \qquad \text{(Formula 3)}$$

The blood flow amount calculation unit 236 substitutes the blood vessel diameter w calculated by the blood vessel diameter calculation unit 235 and the maximum blood flow velocity Vm based on the blood flow velocity calculated by the blood flow velocity calculation unit 234 into this formula to determine the blood flow amount Q. In another example, the blood flow amount calculation unit 236 executes the time integration of the product (or the integrated value) of the chronological change of the blood flow velocity and the blood vessel diameter (or the chronological change thereof) to determine the blood flow amount Q. The unit of the blood flow amount Q is, for example, µL/min.

(Cross Section Setting Unit)

The main controller 211 displays a fundus image on the display unit 241. The fundus image may be an observation image or a photographed image. The fundus image may be any image that constitutes a photographed image. The user operates the operation unit 242 to designate the first cross section C0 in the displayed fundus image. Based on the designated first cross section C0 and the fundus image, the cross section setting unit 237 sets the second cross section C1. As mentioned above, the first cross section C0 is designated such that the first cross section C0 intersects the desired interested blood vessel db.

For example, a pointing device is used to perform the operation of designating the first cross section C0 in the fundus image. When the display unit 241 is a touch panel, the user touches a desired location in the displayed fundus image to designate the first cross section C0. In this case, parameters (e.g., orientation, length) of the first cross section C0 is set manually or automatically.

When setting manually, for example, the user can use a predetermined interface to set the parameters. The interface may include hardware such as a switch, or may include software such as a graphical user interface (GUI).

When setting automatically, for example, the cross section setting unit 237 sets the parameters based on the location designated in the fundus image by the user. A predetermined value of the length may be automatically set. The length may be automatically set based on the designated location and the locations of blood vessels near the designated location. The predetermined value of the length is designated, for example, based on general distance between a predetermined interested blood vessel and blood vessels in the vicinity thereof. Information on the general distance may be generated based on clinical data. This is the same in the case in which the designated location and the locations of the nearby blood vessels. In either case, the length of the first cross section C0 is set so as to intersect the interested blood vessel db and intersect no other blood vessels (in particular, thick blood vessels).

When automatically setting the orientation of the first cross section C0, a predetermined orientation may be set, or the orientation of the interested blood vessel db may be taken into account. In the farmer case, information representing the gradients of a predetermined interested blood vessel at a plurality of locations is generated, and the information is used in the automatic setting. The information may be generated based on clinical data. In the latter case, the running direction of the interested blood vessel db at a designated location is determined, and the orientation of the first cross section C0 is set based on the designated running direction. The designation of the running direction includes thinning of the interested blood vessel db, for example. In either case, the orientation of the first cross section C0 may be set such that the first cross section C0 orthogonally intersects the running direction.

Next, the setting of the second cross section C1 will be described. The cross section setting unit 237 sets the second cross section C1 at a location that is predetermined distance away from the first cross section C0. The predetermined distance is set to 100 µm, for example. The specification of the predetermined distance is carried out in the aforementioned manner, for example. Further, the length and/or the orientation of the second cross section C1 may be set in the same way as for the first cross section C0.

In the present embodiment, the cross sections C0 and C1 (that is, the scan positions of the measurement light LS) are set based on a fundus image. To do so, the correspondence between positions in a fundus image and scan positions is required. In order to obtain the correspondence, it is preferable that, as in the present embodiment, part of the optical system for fundus photography and part of the optical system for OCT are common. With such a coaxial configuration, the common optical axis can be used as a reference to associate the positions in the fundus image with the scan positions. Here, the display magnification of the fundus image, which includes at least any one of so-called optical zooming and digital zooming) may be taken into account to obtain the correspondence.

When such a coaxial configuration is not applied, the positions in a fundus image and scan positions may be associated with each other based on the fundus image and a projection image formed by OCT. The projection image is an image that renders the morphology of the fundus Ef and is created by adding up, along the depth direction (z direction), a three dimensional image acquired through the three dimensional scan (i.e., through the raster scan). Using such a projection image, the positions in the fundus image and the positions in the projection image can be associated with each other by means of image correlation, for example. Such association gives the correspondence between the positions of the fundus image and the scan positions. When taking into account the influence of the eye movement of the eye E (e.g., involuntary eye movement during fixation), it can be thought that the coaxial configuration is more preferable because the acquisition of the fundus image and OCT can be performed with substantially no time lag.

(Monitoring Unit)

The monitoring unit 238 monitors the phase image acquired in real time, thereby determining the start timing of the scan for acquiring blood flow information. To do so, the monitoring unit 238 detects a predetermined time phase of the blood flow by, for example, monitoring the chronological change in the signal intensity in at least a partial region of the phase image. Furthermore, the monitoring unit 238 outputs a predetermined signal (referred to as a scan start signal) at a timing corresponding to the detected predetermined time phase. The scan start signal is input to the controller 210. In response to the reception of the input of the scan start signal, the main controller 211 starts the scan (for example, a first scan or a second scan) for acquiring blood flow information.

A specific example of processing executed by the monitoring unit 238 will be described. As described above, the monitoring unit 238 performs a process of detecting the predetermined time phase (referred to as a time phase detection process) by monitoring the phase image, and a process of outputting the scan start signal according to the detection result (referred to as a signal output process).

An example of the time phase detection process will be described. As the predetermined time phase to be detected, the time phase in which a strong signal can be obtained in the cardiac cycle or the time phase related thereto can be set in advance. For example, it is possible to adopt a time phase of blood flow corresponding to the peak (R wave) of the electro cardiogram indicating the timing at which the ventricle shrinks strongly and blood is delivered from the heart. Alternatively, it is possible to adopt a time phase corresponding to the starting up timing (Q wave) of the electro cardiogram towards the R wave. In another example, it is possible to adopt a time phase (or a time phase immediately thereafter) corresponding to the arrival timing of the pressure applied to the blood flow at the cardiac phase of the R wave at the blood vessel (for example, a certain cross section of the interested blood vessel) of the fundus Ef. In general, the predetermined time phase may be any characteristic time phase of blood flow in the fundus Ef.

The predetermined time phase is detected by monitoring the phase image. The phase image represents the chronological change in the phase difference in the cross section of the fundus Ef (i.e., the cross section that intersects the interested blood vessel). Such a phase image is an image expressing blood flow dynamics (e.g., blood flow direction, blood flow velocity) in the interested blood vessel as signal intensity, and furthermore, it is an image expressing chronological change in the blood flow as chronological change in signal intensity. The chronological change in the signal intensity is expressed as chronological change in the pixel values of the pixels in the phase image. The monitoring unit 238 monitors the chronological change in pixel values of part of or all the pixels constituting the phase image to detect the predetermined time phase. As an example, this process may include a process of detecting a time phase at which the value of the signal intensity (e.g. the absolute value thereof) becomes relatively large (for example, a time phase at which the signal intensity becomes maximum in the cardiac cycle). Alternatively, this process may include a process of detecting a time phase at which the change in the signal intensity (e.g., gradient, differential value) becomes relatively large (for example, a time phase at which the change in the signal intensity becomes maximum in the cardiac cycle). Here, the value or the change in the signal intensity may be a value or a change for a single pixel in the phase image, or it may be statistically calculated from values or changes for two or more pixels in the phase image (e.g., average value, median value, mode value, maximum value, minimum value).

As described above, part or the whole of the phase image can be monitored to detect a predetermined time phase. In the present embodiment, only part of the phase image is monitored. The partial region of the phase image to be monitored includes at least part of the cross section of the interested blood vessel. Such a monitoring target region is specified (or extracted) by the blood vessel region specification unit 231.

Subsequently, signal output processing will be described. The monitoring unit 238 may be configured to output the scan start signal at a timing when the predetermined time phase is detected. Alternatively, the monitoring unit 238 may be configured to output the scan start signal at a timing when a preset length of time has elapsed from the timing at which the predetermined time phase is detected. Such standby time is set in advance or in real time, for example, based on the characteristics of the blood flow dynamics (for example, the length of time between the time phase corresponding to the R wave and the time phase at which scan begins). The scan start signal may be a single signal (e.g., a pulse signal) sent from the monitoring unit 238 to the controller 210, or may be part of a signal sent from the monitoring unit 238 to the controller 210 (e.g., a signal whose transmit start time is before the detection timing of the predetermined time phase or before the generation timing of the scan start signal).

The image processor 230 having the above functions includes, for example, a microprocessor, RAM, ROM, hard disk drive, circuit board, and the like. Computer programs for the microprocessor to execute the above functions are stored, in advance, in the storage device such as the hard disk drive.

(User Interface)

A user interface 240 includes the display unit 241 and the operation unit 242. The display unit 241 includes the aforementioned display device of the arithmetic and control unit 200, the display device 3, and the like. The operation unit 242 includes the aforementioned operation devices of the arithmetic and control unit 200. The operation unit 242 may also include various kinds of buttons, keys, etc. that are arranged on the housing of the blood flow measurement apparatus 1 or are peripheral equipment. For example, when the housing of the fundus camera unit 2 is similar to that of the conventional fundus camera, the operation unit 242 may include a joy stick, an operation panel, etc. arranged on the housing. The display unit 241 may include various kinds of display devices such as a touch panel monitor arranged on the housing of the fundus camera unit 2.

The display unit 241 and the operation unit 242 do not need to be individual devices. For example, like a touch panel, a device having both the display function and the operation function can be employed. In such a case, the operation unit 242 includes a touch panel and computer programs. Contents of operation performed using the operation unit 242 are input into the controller 210 as electrical signals. Further, operation and information input may be carried out using the GUI displayed on the display unit 241 and the operation unit 242.

<Operation>

Examples of the operation of the blood flow measurement apparatus 1 will be described.

First Operation Example

FIG. 7 shows an example of the operation of the blood flow measurement apparatus 1. In this operation example, a case where the first scan and the second scan are executed alternately will be described.

At step 1005 (S1), the preparation for OCT includes the input of patient ID, the selection of an operation mode corresponding to the present embodiment (i.e., blood flow measurement mode), or the like. Subsequently, alignment and focus adjustment are performed. In addition, tracking may be commenced. Furthermore, a fundus image (e.g., an observation image, a photographed image, or an image constituting a photographed image) is displayed on the display unit 241.

Then, at step 1010 (S2), the user designates the location where the blood flow is to be measured in the fundus image displayed. Here, the first cross section is designated. The method of designating the first cross section is described above. Alternatively, the first cross section may be automatically designated with referring to a predetermined site (e.g., optic nerve head) of the fundus Ef. Such automatic designation includes, for example, a process of specifying the predetermined site, a process of specifying the interested blood vessel, a process of setting the first cross section such that the first cross section is apart from the specified predetermined site by a predetermined distance and intersects the specified interested blood vessel. The series of processes is executed by the cross section setting unit 237.

Upon designating the first cross section, the cross section setting unit 237 at step 1015 (S3) sets the second cross section based on the first cross section.

At step 1020 (S4), the main controller 211 controls the light source unit 101, the optical scanner 42, etc. to perform preparatory OCT measurement. The preparatory OCT measurement is applied to the first cross section, the second cross section, or another cross section. Then, it is determined whether an image acquired through the preparatory OCT measurement is adequate or not. The determination may be carried out through the visual observation by the user. Alternatively, the determination may be automatically executed by the blood flow measurement apparatus 1.

When determining through the visual observation, the main controller 211 displays the OCT image on the display unit 241. The user checks the image quality of the OCT image, the displayed location of a predetermined tissue (e.g., blood vessels, the surface of the retina) in the OCT image, or the like. When the OCT image is inadequate, the user adjusts measurement conditions. For example, when the displayed location is inadequate, the user operates the optical path length changer 41 to adjust the optical path length of the measurement light LS. When the image quality is inadequate, the user operates the optical attenuator 105, the polarization controller 106, or the like.

When the determination is automatically executed, the blood flow measurement apparatus 1 evaluates the image quality, the displayed location of the predetermined tissue, etc. with referring to a predetermined evaluation criterion, and adjusts the measurement conditions based on the result of the evaluation in the same manner as in the manual adjustment.

Upon receiving a predetermined trigger (for example, the completion of step 1020 (S4) or an instruction from the user), the main controller 211 starts monitoring the phase image at step 1025 (S5). More specifically, upon receiving the predetermined trigger, the main controller 211 executes control so as to iteratively scan a predetermined cross section of the interested blood vessel with the measurement light LS. Here, the predetermined cross section may be, for example, the first cross section set in step 1010 (S2), the second cross section set in step 1015 (S3), or a cross section other than them. Also, the predetermined cross section is a single cross section or a plurality of cross sections.

Further, the main controller 211 performs control of the following series of processes to be executed in real time. That is, the main controller 211 performs the control of the following series of processes to be executed in parallel with iterative scan of the predetermined cross section. First, the phase image forming unit 222 forms a phase image based on the data acquired through the iterative scan. The blood vessel region specification unit 231 specifies a blood vessel region in the phase image (e.g., in each frame thereof). In order to detect a predetermined time phase of the blood flow, the monitoring unit 238 monitors the chronological change in the signal intensity in at least part of the blood vessel region of the phase image (e.g., of each frame thereof).

At step 1030 (S6), the monitoring process in step 1025 (S5) continues until the predetermined time phase is detected (step 1030 (S6): NO). When the predetermined time phase is detected (step 1030 (S6): YES), the process proceeds to step 1035 (S7).

When the predetermined time phase is detected in step 1030 (S6) (step 1030 (S6): YES), the monitoring unit 238 sends the scan start signal to the controller 210.

In response to the reception of the scan start signal transmitted from the monitoring unit 238 in step 1035 (S7), the main controller 211 starts OCT measurement (i.e., blood flow measurement) in step 1040 (S8). FIG. 8 shows an outline of the processes executed in the present operation example.

The present operation example alternately performs the first scan J1 and the second scan J2. The first scan J1 is the OCT measurement of the first cross section at which blood flow is measured. The second scan J2 is the OCT measurement of the second cross section near the first cross section. The example shown in FIG. 8 alternately performs a single first scan (i.e., a single B scan of the first cross section) and a single second scan (i.e., a single B scan of the second cross section). Through such scans, the followings are acquired: the pair of data [J1, J2]1, acquired through the first scan of the first time and the second scan of the first time; the pair of data [J1, J2]2, acquired through the first scan of the second time and the second scan of the second time; . . . ; the pair of data [J1, J2]n, acquired through the first scan of the n-th time and the second scan of the n-th time. The data pairs [J1, J2]i (i=1 to n) correspond to the times ti (i=1 to n), respectively. Any time point during the OCT measurement to acquire the data pair [J1, J2]i (i=1 to n) is assigned to the time ti (i=1 to n). It is possible to alternately perform one or more times of the first scan and one or more times of the second scan.

The OCT measurement (i.e., blood flow measurement) in step 1040 (S8) is performed over a predetermined period (referred to as a measurement period). The measurement period (that is, the elapsed time from the time t1 to the time tn) may be a period corresponding to one cardiac cycle or a slightly longer period than the cardiac cycle (e.g., 1 second). This is sufficiently shorter than the conventional measurement period (e.g., the measurement period of the present operation example is half of that of the conventional measurement period). Such a shortening of the measurement period is achieved by the characteristic of the present embodiment in which OCT measurement can be performed in synchronization with the heartbeat with the configuration that performs the OCT measurement (in particular, the OCT measurement for calculating the gradient of the interested blood vessel) from the predetermined time phase.

At step 1045 (S9), the image forming unit 220 forms images based on the data acquired in step 1040 (S8). In the present operation example, based on each of the data pairs [J1, J2]i (i=1 to n), the cross sectional image forming unit 221 forms the first cross sectional image T1$i$ (i=1 to n) rendering the first cross section and the second cross sectional image T2$i$ (i=1 to n) rendering the second cross section. The first cross sectional image T1$i$ and the second cross sectional image T2$i$ (i=1 to n) correspond to the time ti (i=1 to n).

In addition, based on the data [J1]i (i=1 to n−1) on the first cross section included in the data pair [J1, J2]i (i=1 to n−1) and the data [J1]i+1 (i=1 to n−1) on the first cross section included in the next data pair [J1, J2]i+1 (i=1 to n−1), the phase image forming unit 222 forms the phase image Pi (i=1 to n−1) rendering the first cross section. The phase image Pi (i=1 to n−1) correspond to the times ti (i=1 to n−1).

The present operation example does not create the phase image Pn corresponding to the time tn; however, the phase image Pn can be created by performing the n+1-th OCT measurement of the first cross section. Alternatively, the phase image Pn may be a copy of the phase image Pn−1. In another example, the first cross sectional image T1$n$ and the second cross sectional image T2$n$ both corresponding to the time tn are not formed. Another example may form one or more representative pairs of the first cross sectional image and the second cross sectional image based on any one or more representative data pairs among the data pairs [J1, J2]i (i=1 to n).

At step 1050 (S10), the blood vessel region specification unit 231 specifies a blood vessel region corresponding to the interested blood vessel for each of the first cross sectional image T1$i$, the second cross sectional image T2$i$, and the phase image Pi.

The gradient calculation unit 232 in step 1055 (S11) calculates the gradient of the interested blood vessel at the first cross section based on the blood vessel regions specified in step 1050 (S10) and the distance between the first cross section and the second cross section (i.e., the cross section interval). As a specific example, based on the cross section interval and two blood vessel regions specified from the first cross sectional image T1$i$ and the second cross sectional image T2$i$ (i=1 to n) at the time ti (i=1 to n), the gradient calculation unit 232 can calculate the gradient Ai (i=1 to n) of the interested blood vessel at the time ti (i=1 to n). Here, in place of the first cross sectional image T1$i$, a blood vessel region specified from the phase image Pi may be used. Instead of calculating the gradient Ai (i=1 to n) corresponding to the time ti (i=1 to n), one or more representative gradient values may be determined.

Based on the chronological change in the phase difference obtained as the phase images Pi (i=1 to n−1) and the gradients Ai (i=1 to n) of the interested blood vessel calculated in step 1055 (S11), the blood flow velocity calculation unit 234 in step 1060 (S12) calculates the blood flow velocity vi (i=1 to n) at the first cross section for the blood flowing through the interested blood vessel. The blood flow velocity values vi (i=1 to n) correspond to the times ti (i=1 to n), respectively. When the phase image Pn is not formed, the blood flow velocity vn may not been calculated.

Based on the first cross sectional images T1$i$ (i=1 to n) or the phase images Pi (i=1 to n−1), the blood vessel diameter calculation unit 235 in step 1065 (S13) calculates the diameter wi (i=1 to n) of the interested blood vessel at the first cross section. In place of determining the blood vessel diameters wi (i=1 to n) corresponding to the times ti (i=1 to n), one or more representative blood vessel diameters may be determined. The blood vessel diameter may be calculated by analyzing fundus images instead of the first cross sectional images.

Based on the blood flow velocity determined in step 1060 (S12) and the blood vessel diameter determined in step 1065 (S13), the blood flow amount calculation unit 236 in step 1070 (S14) calculates the flow amount Q (μL/min) of the blood that flows through the interested blood vessel.

At step 1075 (S15), the main controller 211 displays blood flow information including the blood flow velocity vi calculated in step 1060 (S12), the blood vessel diameter wi calculated in step 1065 (S13), the blood flow amount Q calculated in step 1070 (S14), etc. on the display unit 241. In addition, the main controller 211 associates the blood flow information with the patient ID input in step 1005 (S1), and stores it in the storage unit 212. This terminates the processing of the present operation example.

Second Operation Example

An example of the operation of the blood flow measurement apparatus 1 is shown in FIG. 9. In this operation example, a case where the first scan is executed after executing the second scan will be described.

Steps 1080 (S21) to 1115 (S27) of the present operation example are executed in the same manner as steps 1005 (S1) to 1035 (S7) of the first operation example.

In response to the reception of the scan start signal transmitted from the monitoring unit 238 in step 1115 (S27), the main controller 211 performs control of OCT measurement (i.e., the second scan) at step 1120 (S28) for obtaining the gradient of the blood vessel to be executed. In the present operation example, the second scan is performed in such a manner that each of the two or more cross sections is scanned at least once. As a specific example thereof, as shown in FIG. 6, each of two cross sections including one first cross section and one second cross section can be scanned once (or a plurality of times).

As another example, as shown in FIG. 10, two second cross sections different from the first cross section can be scanned once (or a plurality of times) each. Here, the two second cross sectional images formed in the subsequent stage of processing based on the data acquired through the scan of two second cross sections are denoted by symbols G1 and G2, respectively. Further, the two blood vessel regions specified by the subsequent stage of processing from the second cross sectional images G1 and G2 are denoted by symbols V1 and V2, respectively. The processing of obtaining the gradient A of the interested blood vessel at the first cross section from the blood vessel regions V1 and V2 is executed in the same manner as the processing based on the two blood vessel regions V0 and V1.

In the present operation example, OCT measurement for obtaining the gradient of a blood vessel can be performed at a suitable timing (for example, the timing at which the scan start signal is input) while monitoring the blood flow dynamics. Therefore, performing the OCT measurement a plurality of times is unnecessary unlike the conventional techniques in which such control of timing is impossible. In other words, according to the present operation example, it is sufficient to scan each second cross section once.

At step 1125 (S29), after the completion of the OCT measurement in step 1120 (S28), the main controller 211 executes control for the iterative OCT measurement (i.e., blood flow measurement or Doppler OCT measurement) of the first cross section. It should be noted that the completion of step 1120 (S28) may be or may not be the start trigger of step 1125 (S29). As an example of the latter, step 1125 (S29) may be started when a predetermined length of time has elapsed after the completion of step 1120 (S28). Alternatively, it is possible to configure to restart the monitoring of the phase image after the completion of step 1120 (S28) so as to obtain the start trigger of step 1125 (S29) (i.e., the scan start signal). As in the first operation example, the OCT measurement of the present operation example is performed over a predetermined period (for example, a period corresponding to one cardiac cycle or a slightly longer period than the cardiac cycle). At this stage also, measurement time can be shortened.

At step 1130 (S30), the image forming unit 220 forms images based on the data acquired in step 1120 (S28). This processing includes processing in which the cross sectional image forming unit 221 forms respective cross sectional images of the two or more second cross sections. Further, the image forming unit 220 forms an image based on the data acquired in step 1125 (S29). This processing includes at least processing in which the phase image forming unit 222 forms a phase image of the first cross section. In addition, this processing may include processing in which the cross sectional image forming unit 221 forms a cross sectional image of the first cross section.

The blood vessel region specification unit 231 in step 1135 (S31) specifies a blood vessel region corresponding to the interested blood vessel for each of the two or more cross sectional images and the phase images (and the cross sectional images of the first cross section) formed in step 1130 (S30).

The gradient calculation unit 232 in step 1140 (S32) calculates the gradient of the interested blood vessel at the first cross section based on the blood vessel regions of the two or more cross sectional images specified in step 1135 (S31) and the distance between the two second cross sections. In the example shown in FIG. 10, the cross section interval is set to be 2d.

Based on the phase image formed in step 1130 (S30) and the gradient of the interested blood vessel calculated in step 1140 (S32), the blood flow velocity calculation unit 234 in step 1145 (S33) calculates the blood flow velocity at the first cross section of the blood that flows through the interested blood vessel.

At step 1150 (S34), the blood vessel diameter calculation unit 235 calculates the diameter of the blood vessel region (e.g., the blood vessel region in the phase image or the blood vessel region in the cross sectional image) in the first cross section specified in step 1135 (S31).

Based on the blood flow velocity determined in step 1145 (S33) and the blood vessel diameter determined in step 1150 (S34), the blood flow amount calculation unit 236 in step 1155 (S35) calculates the flow amount of the blood that flows through the interested blood vessel.

At step 1160 (S36), the main controller 211 displays blood flow information including the blood flow velocity calculated in step 1145 (S33), the blood vessel diameter calculated in step 1150 (S34), the blood flow amount calculated in step 1155 (S35), etc. on the display unit 241. In addition, the main controller 211 associates the blood flow information with the patient ID input in step 1135 (S31), and stores it in the storage unit 212. This terminates the processing of the present operation example.

Modifications of Second Operation Example

In the second operation example, the Doppler OCT measurement (i.e., the first scan) is performed after the OCT measurement (i.e., the second scan) for obtaining the gradient of the blood vessel. On the other hand, a configuration may be employed in which the second scan is performed after the first scan. In addition, the start trigger of the second scan after the first scan may be the same as the second operation example.

<Effects>

Effects of the blood flow measurement apparatus of the present embodiment will be described.

The blood flow measurement apparatus of the present embodiment is an apparatus configured for acquiring blood flow information on an interested blood vessel of a living body, and includes a scanner, an image forming unit, an image processor, and a controller.

The scanner is configured to scan a cross section that intersects the interested blood vessel using OCT. In the present embodiment, the scanner includes at least the optical system for performing OCT measurement. For example, the optical path of the measurement light LS shown in FIG. 1 and the optical system shown in FIG. 2 are included.

The image forming unit is configured to form an image of the cross section based on the data acquired through the scan. In the present embodiment, the image forming unit 220 functions as the image forming unit.

The image processor is configured to process the image formed by the image forming unit. In the present embodiment, the image processor 230 functions as the image processor.

The controller controls the scanner to iteratively scan one or more cross sections (e.g., the first cross section, the second cross section, or any other cross section) of the interested blood vessel. Based on the data acquired through the iterative scan, the image forming unit forms a phase image that represents chronological change in phase difference in the cross section. The image processor outputs a predetermined signal (i.e., the scan start signal) based on the chronological change in the phase difference represented by the phase image. In response to the reception of the scan start signal, the controller controls the scanner to start scan (i.e., the first scan or the second scan) for acquiring blood flow information. The blood flow information is generated based on the data acquired through the scan.

With such a blood flow measurement apparatus, it is possible to actually detect the time phase of blood flow. Here, the time phase is substantially synchronized with the cardiac phase. In addition, it is possible to start OCT measurement for acquiring the blood flow information in accordance with the time phase detection. As a result, time taken to perform blood flow measurement can be shortened. Such an effect is based on the technical idea of the present embodiment which is completely different from the conventional techniques. Note that the conventional techniques acquire data necessary for generating blood flow information by taking the length of the measurement period into account, and do not actually detect the time phase.

In the present embodiment, the image processor may include a monitoring unit configured for outputting the scan start signal. The monitoring unit detects a predetermined time phase of the blood flow by monitoring the chronological change in the signal intensity in at least a partial region of the phase image, and outputs the scan start signal at a timing corresponding to the predetermined time phase detected. Further, the monitoring unit may be configured to monitor the chronological change in the signal intensity in at least part of the blood vessel region in the phase image corresponding to the interested blood vessel. As a result, labor in the process of monitoring the phase image can be saved.

Although it is conceivable to utilize an electrocardiograph, a pulse monitor, a pulse oximeter, or the like in order to detect the time phase of the blood flow, it is difficult to say that the utilization of such a device is preferable due to the following disadvantages: the fact that a dedicated device to detect the time phase needs to be provided; the fact that it takes time and labor to attach electrodes to the subject; the fact that a configuration for connecting such a device to the blood flow measurement apparatus is required; the fact that a configuration for processing signals from such a device is needed; and the fact that there is a possibility that a time lag may exist between the time phase detected by such a device and the time phase related to the blood flow in eye fundus. On the other hand, the present embodiment has an advantage that the time phase of the interested blood vessel can be detected without providing an electrocardiograph, a pulse monitor, a pulse oximeter, or the like.

In the present embodiment, the controller may be configured to control the scanner to perform, as the scan for acquiring the blood flow information, first scan that iteratively scans a first cross section of the interested blood vessel and second scan that scans two or more second cross sections. Here, at least one of the two or more second cross sections is different from the first cross section. When such a configuration is employed, the image forming unit forms a phase image that represents the chronological change in the phase difference in the first cross section based on the data acquired through the first scan, and forms two or more images of the two or more second cross sections based on the data acquired through the second scan. In addition, the image processor may include a blood vessel region specification unit (231), a gradient calculation unit (232), and a blood flow information generation unit (233). The blood vessel region specification unit is configured to specify a first blood vessel region corresponding to the interested blood vessel in the phase image of the first cross section, and specify two or more second blood vessel regions corresponding to the interested blood vessel in the two or more image of the two or more second cross sections. The gradient calculation unit is configured to calculate the gradient of the interested blood vessel at the first cross section based on the two or more second blood vessel regions. The blood flow information generation unit is configured to generate the blood flow information based on the first blood vessel region in the phase image of the first cross section and the gradient of the interested blood vessel.

As a specific example of such a configuration, the controller may be configured to, upon receiving the scan start signal, control the scanner to alternately perform the first scan and the second scan (see the first operation example described above).

Alternatively, the controller may be configured to, upon receiving the scan start signal, control the scanner to start the second scan, and to start the first scan after the completion of the second scan (see the second operation example described above). Conversely, the controller may be configured to, upon receiving the scan start signal, control the scanner to start the first scan, and to start the second scan after the completion of the first scan (see the modification example of the second operation example described above).

In the present embodiment, the blood flow information generation unit may include a blood flow velocity calculation unit. The blood flow velocity calculation unit is configured to determine the chronological change in the blood flow velocity at the first cross section for the blood flowing through the interested blood vessel based on the first blood vessel region in the phase image of the first cross section and the gradient of the interested blood vessel.

In addition, the blood flow information generation unit may include a blood vessel diameter calculation unit and a blood flow amount calculation unit. The blood vessel diameter calculation unit is configured to calculate the diameter of the interested blood vessel at the first cross section based on an image formed based on data acquired through scan of the first cross section. The blood flow amount calculation unit is configured to calculate the blood flow amount of the blood flowing through the interested blood vessel based on the chronological change in the blood flow velocity and the diameter of the interested blood vessel.

Second Embodiment

The first embodiment describes the configurations focusing on the timing of starting OCT measurement for acquiring the blood flow information. On the other hand, in the second embodiment, the configurations focusing on the timing of terminating the OCT measurement will be described.

The blood flow measurement apparatus of the second embodiment has a similar configuration to that of the first embodiment. Hereinafter, the drawings of the first embodiment will be referred to.

When the OCT measurement for acquiring the blood flow information is started, the main controller 211 sequentially stores the data obtained by the OCT measurement in the storage unit 212. In the present embodiment, the storage unit 212 may include a temporary storage device that is configured to sequentially update (overwrite) input data and store the data. An example of such a temporary storage device is a ring buffer. The ring buffer, which is also called a circular buffer, is configured to be a data structure using a single and fixed-size buffer, and is configured as if the both ends of the data structure are connected. The size of the ring buffer may be arbitrary. For example, the ring buffer is configured to be capable of storing data obtained for 2 seconds in the iterative OCT measurement for acquiring the blood flow information. In such a ring buffer, data obtained during the latest 2 seconds is always stored.

Note that the data stored in the ring buffer may be data (i.e., detection signals) output from the optical detector 115, or may be data obtained by processing the detection signals. Examples of the latter include a plurality of A scan profiles (i.e., reflection intensity profiles) obtained through B scan (of the first cross section), a plurality of A scan images based on the A scan profiles, and a B scan image based on the A scan images.

The operation of the blood flow measurement apparatus of the present embodiment will be described. An example of the operation is shown in FIG. 11. It should be noted that the measurement preparation (the input of the patient ID, the selection of an operation mode, etc.) described in the first embodiment has already been performed. Further, alignment, focusing, tracking, etc. may be performed in advance or may be performed in real time. For example, the operation according to the present embodiment may be performed after alignment etc., or may be performed together with alignment etc. It is assumed that the process of displaying on the display unit 241 the fundus image (e.g., the observation image, the photographed image, or the image constituting the photographed image) and the image acquired by preliminary OCT measurement has already been started. Furthermore, it is assumed that the designation of the measurement position (e.g., the designation of the first cross section and the second cross section) or the like has already been performed.

At step 1165 (S41), the OCT measurement for acquiring blood flow information is started. For example, the OCT measurement begins with the OCT measurement for obtaining the orientation of the interested blood vessel, and then the iterative OCT measurement (i.e., the iterative OCT measurement of the first cross section) for acquiring the phase image is started.

When the OCT measurement is started in step 1165 (S41), the main controller 211 sequentially stores the data sequentially acquired through the iterative OCT measurement in the storage unit 212 (e.g., the ring buffer) in step 1170 (S42). The data stored in the ring buffer is limited to that based on the iterative OCT measurement for acquiring the phase image. Therefore, the data for obtaining the orientation of the interested blood vessel is stored in the area of the storage unit 212 other than the ring buffer.

At step 1175 (S43), when a predetermined length of time (for example, 2 seconds) elapses from the start of the data storage in step 1170 (S42), the data stored first among the data currently stored in the ring buffer is to be updated (overwritten) with the newly acquired data. Such an updating process is executed for each new acquisition of data. With this, at an arbitrary timing, the state in which the ring buffer stores the latest 2 seconds of data is achieved.

The user observes the displayed fundus image, the OCT image, etc., and grasps the movement of the eye E. Then, at a timing when the user has determined that the eye E has not moved for a predetermined time (for example, 2 seconds), the user inputs a predetermined instruction using the operation unit 242 in step 1180 (S44). The instruction may be, for example, an instruction to terminate the OCT measurement for acquiring blood flow information, or an instruction to start the process of generating blood flow information. Upon receiving the operation from the user, the operation unit 242 sends an operation signal to the controller 210.

At step 1185 (S45), upon receiving the operation signal output from the operation unit 242 in step 1180 (S44), the main controller 211 reads out all the data stored at the present time in the ring buffer. Then, the main controller 211 sends the data read out from the ring buffer to the image forming unit 220.

When the data stored in the ring buffer is image data, that is, when the data stored in the ring buffer is data formed by the image forming unit 220, the main controller 211 sends the data read out from the ring buffer to the image processor 230.

In addition, at the present stage (or at an arbitrary timing earlier than the present stage), the main controller 211 sends data for determining the orientation of the interested blood vessel to the image forming unit 220 or the image processor 230.

At step 1190 (S46), the image forming unit 220 forms an image based on the data read out in step 1185 (S45). This processing includes at least a process in which the phase image forming unit 222 forms a phase image from the data. Furthermore, at the present stage (or at an arbitrary timing earlier than the present stage), the cross sectional image forming unit 221 executes processing of forming a cross sectional image from the data for obtaining the orientation of the interested blood vessel.

At step 1195 (S47), the image processor 230 generates blood flow information based on the phase image and the cross sectional image formed in step 1190 (S46). This processing is executed in the same manner as in the first embodiment (see steps 1050 (S10) to 1070 (S14) in FIG. 7).

At step 1200 (S48), the main controller 211 displays the blood flow information generated in step 1195 (S47) on the display unit 241. In addition, the main controller 211 associates the blood flow information with the patient ID and stores it in the storage unit 212. This terminates the processing of the present operation example.

Effects of the blood flow measurement apparatus of the present embodiment will be described.

The blood flow measurement apparatus of the present embodiment is configured for acquiring blood flow information on an interested blood vessel of a living body. The blood flow measurement apparatus includes a scanner, an image forming unit, an image processor, a storage unit, an instruction input unit, and a controller. The scanner, the image forming unit, and the image processor are the same as those in the first embodiment.

The storage unit is configured to store the data acquired by the scanner. In the present embodiment, the storage unit 212 functions as the storage unit. The storage unit may be a ring buffer or the like. The instruction input unit is configured for inputting a user's instruction. In the present embodiment, the user interface 240 (in particular, the operation unit 242) functions as the instruction input unit. The controller executes processing described below. In the present embodiment, the controller 210 (in particular, the main controller 211) functions as the controller.

The controller controls the scanner to start iterative scan of one or more cross sections of the interested blood vessel. In response to the start of the iterative scan, the data sequentially acquired by the iterative scan is stored in the storage unit in a sequential order.

In addition, upon receiving the user's instruction input using the instruction input unit, the controller reads out data that is stored in the storage unit during a period between an input timing of the user's instruction and a timing before the input timing by a predetermined time length. Note that the user can input an instruction at a timing when the user has determined that the subject's eye has not moved for at least a predetermined time. The predetermined time is set to a length equal to or longer than the data acquisition time required for generating the blood flow information. The predetermined time can be set, for example, to 2 seconds or less.

The image forming unit forms a phase image(s) in one or more cross sections of the interested blood vessel based on the data read out from the storage unit by the control unit. As in the first embodiment, the phase image is an image that represents the chronological change in the phase difference in the cross section.

The image processor generates the blood flow information of the interested blood vessel based on the phase image formed by the image forming unit.

According to such an embodiment, the blood flow information can be generated based on the data acquired during a period in which the user has determined that the subject's eye has not moved. Therefore, the possibility of having to reperform the measurement can be reduced. In addition, time taken to perform blood flow measurement can be shortened by appropriately setting the acquisition time of the data read out by the controller. (e.g., by appropriately setting the predetermined time described above)

It should be noted that the user determines that the subject's eye has not moved over the predetermined time in the present embodiment; however, it is possible to employ a configuration in which the blood flow measurement apparatus executes the determination. For example, the blood flow measurement apparatus may be configured to detect the movement of the subject's eye by analyzing an anterior segment image, a fundus image or an OCT image acquired in real time, and perform the data read out process described above when the blood flow measurement apparatus determines that the subject's eye has not moved over the predetermined time.

Modification Examples

The configurations described above are merely examples for implementing the present invention. Therefore, it is possible to make arbitrary modification (omission, replacement, addition, etc.) within the scope of the present invention.

A modification example of method of calculating blood flow amount will be described. In the present modification example, the blood flow velocity calculation unit 234 generates information (blood flow velocity variation information) that represents chronological change in the blood flow velocity for each pixel included in the blood vessel region in the phase image. The generation of the blood flow velocity variation information may include: a position matching between a plurality of phase images arranged in time series order in a pixel-to-pixel manner (i.e., for each pixel position); and a process of generating the blood flow velocity variation information based on the plurality of pixels arranged in time series order corresponding to each pixel position. With such processing, the blood flow velocity can be determined for each position in the blood vessel region of the first cross section.

The blood flow amount calculation unit 236 calculates the blood flow amount for each pixel through time integration of the blood flow velocity variation information for the pixel included in the blood vessel region. With this processing, the blood flow amount can be determined for each point in the blood vessel region in the first cross section.

Further, the blood flow amount calculation unit 236 can calculate the flow amount of the blood flowing through the interested blood vessel by adding the blood flow amounts for these pixels. With this processing, the blood flow amounts for the plurality of pixels obtained in the prior stage are added together to determine the total amount of the blood that flows within the blood vessel region of the first cross section.

In the above embodiment, the optical path length difference between the optical path of the measurement light LS and the optical path of the reference light LR is changed by varying the position of the optical path length changer 41; however, a method of changing the optical path length difference is not limited to this. For example, it is possible to change the optical path length difference by providing a reflection mirror (i.e., reference mirror) in the optical path of the reference light, and moving the reference mirror in the advancing direction of the reference light to change the optical path length of the reference light. Alternatively, the optical path length difference may be changed by moving the fundus camera unit 2 and/or the OCT unit 100 with respect to the eye E to change the optical path length of the measurement light LS. In another example, if an object to be measured is not a site of a living body or the like, it can be configured to change the optical path length difference by moving the object in the depth direction (i.e., the z direction).

What is claimed is:

1. A method of acquiring blood flow information on an interested blood vessel of a living body, the method comprising:

applying a first iterative scan to one or more cross sections of the interested blood vessel using optical coherence tomography;

forming a phase image representing a chronological change in phase difference in the one or more cross sections, from data acquired by the first iterative scan;

detecting a predetermined time phase of blood flow in the interested blood vessel by monitoring the chronological change in signal intensity of at least part of a blood vessel region in the phase image corresponding to the interested blood vessel;

generating a scan start signal at a timing corresponding to the detected predetermined time phase;

applying a second iterative scan to one or more cross sections of the interested blood vessel using optical coherence tomography in response to the scan start signal; and generating blood flow information on the interested blood vessel, from data acquired by the second iterative scan, wherein the second iterative scan comprises a first scan that iteratively scans a first cross section of the interested blood vessel and a second scan that scans two or more second cross sections, wherein at least one of the two or more second cross sections is different from the first cross section, and the generating blood flow information on the interested blood vessel comprises:

forming a phase image that represents chronological change in phase difference in the first cross section, from data acquired by the first scan;

forming two or more images of the two or more second cross sections, from data acquired by the second scan;

specifying a first blood vessel region corresponding to the interested blood vessel in the phase image of the first cross section;

specifying two or more second blood vessel regions corresponding to the interested blood vessel in the two or more images of the two or more second cross sections;

calculating a gradient of the interested blood vessel at the first cross section based on the two or more second blood vessel regions; and generating blood flow information based on the first blood vessel region in the phase image of the first cross section and the gradient of the interested blood vessel.

2. The method of claim 1, wherein the first scan and the second scan are alternately performed in response to the scan start signal.

3. The method of claim 2, wherein the second scan is applied to two second cross sections, one of the two second cross sections being the first cross section.

4. The method of claim 1, wherein the second scan is started in response to the scan start signal and the first scan is started after completion of the second scan.

5. The method of claim 1, wherein the first scan is started in response to the scan start signal and the second scan is started after completion of the first scan.

6. The method of claim 1, wherein the generating blood flow information on the interested blood vessel comprises calculating chronological change in blood flow velocity at the first cross section for blood flowing in the interested blood vessel based on the first blood vessel region in the phase image of the first cross section and the gradient of the interested blood vessel.

7. The method of claim 6, wherein the generating blood flow information on the interested blood vessel comprises:
   calculating diameter of the interested blood vessel at the first cross section based on an image formed from data acquired by scanning the first cross section; and
   calculating blood flow amount of blood flowing in the interested blood vessel based on the chronological change in blood flow velocity and the diameter of the interested blood vessel.

* * * * *